US007052836B2

(12) United States Patent
Morrison et al.

(10) Patent No.: US 7,052,836 B2
(45) Date of Patent: May 30, 2006

(54) NUCLEIC ACIDS FOR DETECTING FUSARIUM SPECIES

(75) Inventors: Christine J. Morrison, Decatur, GA (US); Errol Reiss, Chamblee, GA (US); Jong Soo Choi, Taegu (KR); Liliana Aidorevich, Maracay Edo Aragua (VE)

(73) Assignee: The Government of the United States of America as represented by the Secretary of the Department of Health and Human Services, Washington, DC (US)

( * ) Notice: Subject to any disclaimer, the term of this patent is extended or adjusted under 35 U.S.C. 154(b) by 543 days.

(21) Appl. No.: 10/046,955

(22) Filed: Jan. 14, 2002

(65) Prior Publication Data

US 2003/0129600 A1   Jul. 10, 2003

Related U.S. Application Data

(62) Division of application No. 09/423,233, filed as application No. PCT/US98/08926 on May 1, 1997, now Pat. No. 6,372,430.

(60) Provisional application No. 60/045,400, filed on May 2, 1997.

(51) Int. Cl.
*C07H 21/04* (2006.01)
*C12Q 1/68* (2006.01)

(52) U.S. Cl. .......................... 435/6; 435/91.1; 435/91.2; 536/23.1; 536/24.32

(58) Field of Classification Search .................... 435/6; 536/23.1, 24.3
See application file for complete search history.

(56) References Cited

U.S. PATENT DOCUMENTS 5,426,027 A   6/1995   Lott et al.
5,585,238 A   12/1996   Ligon et al.
5,958,693 A   9/1999   Sanhu et al.

FOREIGN PATENT DOCUMENTS

WO   WO 95/29260   * 11/1995
WO   WO 96/21741     7/1996

OTHER PUBLICATIONS

Duggal, A. "Fusarium solani 5.8S rRNA gene." Genbank Accession No. U38558, Nov. 1995.*
Duggal, A. "Fusarium oxysporum 5.8S rRNA gene." Genbank Accession No. U28159, Jun. 1995.*
Borsuk et al., GenBank Accession No. U03521, Feb. 1995.
Borsuk et al., GenBank Accession No. U03523, Feb. 1995.
Borsuk et al., GenBank Accession No. U03519, Feb. 1995.
Gaskell et al., "Analysis of the Internal transcribed spacer regions of ribosomal DNA in common airborne allergenic fungi," *Electrophoresis*, vol. 18, pp. 1567-1569 (1997).
Geiser et al., GenBank Accession No. L76747, Nov. 1996.
Geiser et al., GenBank Accession No. L76748, Nov. 1996.
Geiser et al., GenBank Accession No. L76774, Nov. 1996.
Kumeda et al., "Single-stranded conformation polymorphism analysis of PCr-amplified ribosomal DNA ITS to differentiate species of Aspergillus section flavi," *Microbiology*, vol. 62, No. 8, pp. 2947-2952 (1996).
LoBuglio et al., "Phylogeny and PCr identification of the human pathogenic fungus *Penicillium marneffei*," *J. Clinical Microbiol.*, vol. 33, No. 1, pp. 85-89 (1995).
Lu et al., "Typing of *Pneumocystis carinii* Strain with Type-Specific Oligonucleotide Probes Derived from Nucleotide Sequences of Internal Transcribed Spacers of rRNA Genes," *J. Clinical Microbiol.*, vol. 33, No. 11, pp. 2973-2977 (1995).
White et al., "Amplification and direct sequencing of fungal ribosomal RNA genes for phylogenetics", *PCR Protocols: A guide to Methods and Applications*, pp. 315-322 (1989).

* cited by examiner

*Primary Examiner*—Jeanine A. Goldberg
(74) *Attorney, Agent, or Firm*—Klarquist Sparkman, LLP

(57) ABSTRACT

Nucleic acids for detecting *Aspergillus* species and other filamentous fungi are provided. Unique internal transcribed space 2 coding regions permit the development of nucleic acid probes specific for five different species of *Aspergillus*, three species of *Fusarium*, four species of *Mucor*, two species of *Penecillium*, five species of *Rhizopus*, one species of *Rhizomucor*, as well as probes for *Absidia corymbifer, Cunninghamella elagans, Pseudallescheria boydii*, and *Sporothrix schenkii*. Methods are disclosed for the species-specific detection and diagnosis of infection by *Aspergillus, Fusarium, Mucor, Penecillium, Rhizomucor, absidia, Cunninghaemella, Pseudallescheria* or *Sporthrix* in a subject. Furthermore, genus-specific probes are also provided for *Aspergillus, Fusarium* and *Mucor*, in addition to an all-fungus nucleic acid probe.

20 Claims, No Drawings

NUCLEIC ACIDS FOR DETECTING FUSARIUM SPECIES

PRIORITY CLAIM

This is a divisional of U.S. patent application Ser. No. 09/423,233 filed Jun. 27, 2000, issued as U.S. Pat. No. 6,372,430. U.S. patent application Ser. No. 09/423,233 is a § 371 national stage of PCT/US98/08926 filed May 1, 1997, and claims the benefit of U.S. Provisional Application No. 60/045,400 filed May 2, 1997.

This invention was made in the Centers for Disease Control Mycotic Diseases Laboratories, an agency of the United States Government.

TECHNICAL FIELD

This application relates in general to the field of diagnostic microbiology. In particular, the invention relates to the species-specific detection of *Aspergillus, Fusarium, Mucor, Penicillium, Rhizopus, Rhizomucor, Absidia, Cunninghamella, Pseudallescheria boydii* (*Scedosporium apiospermum*), and *Sporothrix* species.

BACKGROUND OF THE INVENTION

In recent years, chemotherapy for hematological malignancies, and high-dose corticosteroid treatment for organ transplant recipients, along with the spread of AIDS, have greatly increased the number of immunocompromised patients (1, 12, 14, 43). Saprophytic filamentous fungi, such as *Aspergillus, Rhizopus,* and *Mucor* species, found in the environment and considered to be of low virulence, are now responsible for an increasing number of infections in the immunocompromised host (17, 20, 43). In addition, these infections are often fulminant and rapidly fatal in immunocompromised patients (7, 11, 12, 20, 44). Morbidity and mortality is extremely high; for example, aspergillosis has a mortality rate of approximately 90% (8, 11).

To complicate matters, diagnosis is difficult and symptoms are often non-specific (18, 27, 29, 42, 44). Antibody-based tests can be unreliable due to the depressed or variable immune responses of immunocompromised patients (2, 9, 18, 46). Antigen detection tests developed to date have fallen short of the desired sensitivity (2, 9, 38). Radiographic evidence can be non-specific and inconclusive (5, 29, 36), although some progress in diagnosis has been made with the advent of computerized tomography (40). However, definitive diagnosis still requires either a positive blood or tissue culture or histopathological confirmation (3, 21). An added complication is that the invasive procedures necessary to obtain biopsy materials are often not recommended in thrombocytopenic patient populations (37, 41).

Even when cultures of blood, lung or rhinocerebral tissues are positive, morphological and biochemical identification of filamentous fungi can require several days for adequate growth and sporulation to occur, delaying targeted drug therapy. Some atypical isolates may never sporulate, making identification even more difficult (23). When histopathology is performed on tissue biopsy sections, the morphological similarities of the various filamentous fungi in tissue make differentiation difficult (16). Fluorescent antibody staining of histopathological tissue sections is not specific unless cross-reactive epitopes are absorbed out which can make the resultant antibody reactions weak (14, 19). Therapeutic choices vary (7, 41, 44) making a test to rapidly and specifically identify filamentous fungi urgently needed for the implementation of appropriately targeted therapy. Early and accurate diagnosis and treatment can decrease morbidity and increase the chances for patient survival (6, 27, 39). Furthermore, identification of filamentous fungi to at least the species level would be epidemiologically useful (24, 31, 43, 47).

PCR-based methods of detection, which show promise as rapid, sensitive means to diagnose infections, have been used in the identification of DNA from *Candida* species (13, 15, 30) and some other fungi, particularly *Aspergillus* species (31, 33, 45). However, most of these tests are only genus-specific (28, 38) or are directed to detect only single-copy genes (4, 35). Others have designed probes to detect multi-copy genes so as to increase test sensitivity (31, 33) but in doing so have lost test specificity because they have used highly conserved genes, which detect one or a few species but which are also plagued with cross-reactivities to human, fungal or even viral DNA (25, 31, 33).

Therefore, it is an object of the invention to provide improved materials and methods for detecting and differentiating *Aspergillus* and other filamentous fungal species in the clinical and laboratory settings.

SUMMARY OF THE INVENTION

The present invention relates to nucleic acids for detecting *Aspergillus, Fusarium, Mucor, Penicillium, Rhizopus, Rhizomucor, Absidia, Cunninghamella, Pseudallescheria* (*Scedosporium*), and *Sporothrix* species. Unique internal transcribed spacer 2 coding regions permit the development of probes specific for five different *Aspergillus* species, *A. flavus, A. fumigatus, A. niger, A. terreus,* and *A. nidulans*. The invention thereby provides methods for the species-specific detection and diagnosis of *Aspergillus* infection in a subject. In addition, species probes have been developed for three *Fusarium*, four *Mucor*, two *Penicillium*, five *Rhizopus* and one *Rhizomucor* species, as well as probes for *Absidia corymbifera, Cunninghamella elegans, Pseudallescheria boydii* (*Scedosporium apiospermum*), and *Sporothrix schenckii*. Generic probes for *Aspergillus, Fusarium,* and *Mucor* species have also been developed.

These and other objects, features and advantages of the present invention will become apparent after a review of the following detailed description of the disclosed embodiments and the appended claims.

DETAILED DESCRIPTION OF THE INVENTION

This invention provides a simple, rapid, and useful method for differentiating filamentous fungal species from each other and from other medically important fungi. This invention enables a rapid, simple and useful method to isolate fungal DNA from host samples, and to apply the species- and genus-specific probes for the diagnosis of a disease. Ultimately, these probes can be used for in situ hybridization or in situ PCR diagnostics so that the morphology of host tissue, and microorganisms, remain intact.

The invention provides nucleic acids containing regions of specificity for five *Aspergillus*, three *Fusarium*, four *Mucor*, two *Penicillium*, five *Rhizopus* and one *Rhizomucor* species as well as probes for *Absidia corymbifera, Cunninghamella elegans, Pseudallescheria boydii* (*Scedosporium apiospremum*), and *Sporothrix schenckii*. These nucleic acids are from the internal transcribed spacer 2 ("ITS2") region of ribosomal deoxyribonucleic acid (rDNA) of the genome of the aforementioned filamentous fungi. The ITS2 region is located between the 5.8S rDNA region and the 28S rDNA region.

In particular, the invention provides nucleic acids from *Aspergillus flavus* (SEQ ID NO:1), *Aspergillus fumigatus* (SEQ ID NO:2), *Aspergillus niger* (SEQ ID NO:3), *Aspergillus terreus* (SEQ ID NO:4), *Aspergillus nidulans* (SEQ ID NO:5), *Fusarium solani* (SEQ ID NO:6), *Fusarium moniliforme* (SEQ ID NO:7), *Mucor rouxii* (SEQ ID NO:8), *Mucor racemosus* (SEQ ID NO:9), *Mucor plumbeus* (SEQ ID NO:10), *Mucor indicus* (SEQ ID NO:11), *Mucor circinilloides f. circinelloides* (SEQ ID NO:12), *Rhizopus oryzae* (SEQ ID NO:13 and NO:14), *Rhizopus microsporus* (SEQ ID NO:15 and 16), *Rhizopus circinans* (SEQ ID NO:17 and 18). *Rhizopus stolonifer* (SEQ ID NO:19), *Rhizomucor pusillus* (SEQ ID NO:20), *Absidia corymbifera* (SEQ ID NO:21 and 22), *Cunninghamella elegans* (SEQ ID NO:23), *Pseudallescheria boydii* (teleomorph of *Scedosporium apiospermum*) (SEQ ID NO:24, 25, 26, and 27), *Penicillium notatum* (SEQ ID NO:28), and *Sporothrix schenkii* (SEQ ID NO:29). These sequences can be used to identify and distinguish the respective species of *Aspergillus, Fusarium, Mucor, Rhizopus,* and *Penicillium,* and identify and distinguish these species from each other and from *Absidia corymbifera, Cunninghamella elegans, Pseudallescheria boydii (Scedosporium apiospermum),* and *Sporothrix schenkii.*

Furthermore, the invention provides isolated nucleic acid probes derived from GenBank nucleic acid sequences (for *Penicillium marneffei* and *Fusarium oxysporum* only) or from the above nucleic acid sequences which may be used as species-specific identifiers of *Aspergillus flavus* (SEQ ID NO:30 and 31), *Aspergillus fumigatus* (SEQ ID NO:32), *Aspergillus niger* (SEQ ID NO:33), *Aspergillus terreus* (SEQ ID NO:34), *Aspergillus nidulans* (SEQ ID NO: 35), *Mucor rouxii* (SEQ ID NO:36), *Mucor plumbeus* (SEQ ID NO:37), *Mucor indicus* (SEQ ID NO:38), *Mucor circinilloides f. circinelloides* (SEQ ID NO:39), *Mucor racemosus* (SEQ ID NO:40), *Rhizopus oryzae* (SEQ ID NO:41), *Rhizopus circinans* (SEQ ID NO:42), *Rhizomucor pusillus* (SEQ ID NO:43), *Rhizopus stolonifer* (SEQ ID NO:44), *Pseudallescheria boydii (Scedosporium apiospermum)* (SEQ ID NO:45), *Penicillium notatum* (SEQ ID NO:46), *Penicillium marneffei* (SEQ ID NO:47 and 48), *Fusarium moniliforme* (SEQ ID NO:49), *Fusarium oxysporum* (SEQ ID NO:50), *Fusarium solani* (SEQ ID NO:51), *Cunninghamella elegans* (SEQ ID NO:52, 53, and 54), *Absidia corymbifera* (SEQ ID NO:55), *Sporothrix schenkii* (SEQ ID NO:56), and *Rhizopus microsporus* (SEQ ID NO:57). Such probes can be used to selectively hybridize with samples containing nucleic acids from species of *Aspergillus, Fusarium, Mucor, Rhizopus* (or *Rhizomucor), Penicillium,* or from *Absidia corymbifera, Cunninghamella elegans, Pseudallescheria boydii (Scedosporium apiospermum),* and *Sporothrix schenkii.* These fungi can be detected after polymerase chain reaction or ligase chain reaction amplification of fungal DNA and specific probing of amplified DNA with DNA probes labeled with digoxigenin, reacted with anti-digoxigenin antibodies labeled with horseradish peroxidase and a colorimetric substrate, for example. Additional probes can routinely be derived from the sequences given in SEQ ID NOs:1–29, which are specific for the respective species. Therefore, the probes shown in SEQ ID NOs:30–57 are only provided as examples of the species-specific probes that can be derived from SEQ ID NOs:1–29.

Generic probes for *Aspergillus* (SEQ ID NO:58), *Fusarium,* (SEQ ID NO:59) and *Mucor* (SEQ ID NO:60) species have also been developed to identify all members of their respective species which are listed above as well as an all fungus biotinylated probe (SEQ ID NO:61) to capture all species-specific and generic probes listed above for their detection.

By "isolated" is meant nucleic acid free from at least some of the components with which it naturally occurs. By "selective" or "selectively" is meant a sequence which does not hybridize with other nucleic acids to prevent adequate determination of an *Aspergillus, Fusarium, Mucor, Penicillium, Rhizopus* or *Rhizomucor* genus or species or of *Absidia corymbifera, Cunninghamella elegans, Pseudallescheria boydii (Scedosporium apiospermum),* or *Sporothrix schenckii* species.

The hybridizing nucleic acid should have at least 70% complementarity with the segment of the nucleic acid to which it hybridizes. As used herein to describe nucleic acids, the term "selectively hybridizes" excludes the occasional randomly hybridizing nucleic acids and thus has the same meaning as "specifically hybridizing". The selectively hybridizing nucleic acids of the invention can have at least 70%, 80%, 85%, 90%, 95%, 97%, 98%, and 99% complementarity with the segment of the sequence to which it hybridizes.

The invention contemplates sequences, probes and primers which selectively hybridize to the complementary, or opposite, strand of DNA as those specifically provided herein. Specific hybridization with nucleic acid can occur with minor modifications or substitutions in the nucleic acid, so long as functional species-specific or genus-specific hybridization capability is maintained. By "probe" is meant nucleic acid sequences that can be used as probes or primers for selective hybridization with complementary nucleic acid sequences for their detection or amplification, which probes can vary in length from about 5 to 100 nucleotides, or preferably from about 10 to 50 nucleotides, or most preferably about 18 nucleotides. The invention provides isolated nucleic acids that selectively hybridize with the species-specific nucleic acids under stringent conditions and should have at least 5 nucleotides complementary to the sequence of interest. See generally, Maniatis (26).

If used as primers, the invention provides compositions including at least two nucleic acids which hybridize with different regions so as to amplify a desired region. Depending on the length of the probe or primer, target region can range between 70% complementary bases and full complementarity and still hybridize under stringent conditions. For example, for the purpose of diagnosing the presence of the *Aspergillus,* the degree of complementarity between the hybridizing nucleic acid (probe or primer) and the sequence to which it hybridizes (e.g., *Aspergillus* DNA from a sample) is at least enough to distinguish hybridization with a nucleic acid from other yeasts and filamentous fungi. The invention provides examples of nucleic acids unique to each filamentous fungus in the listed sequences so that the degree of complementarity required to distinguish selectively hybridizing from nonselectively hybridizing nucleic acids under stringent conditions can be clearly determined for each nucleic acid.

Alternatively, the nucleic acid probes can be designed to have homology with nucleotide sequences present in more than one species of the fungi listed above. Such a nucleic acid probe can be used to selectively identify a group of species such as the generic probes listed for *Aspergillus* (SEQ ID NO:58), *Fusarium* (SEQ ID NO:59), and *Mucor* (SEQ ID NO:60) as well as all fungi listed (SEQ ID NO:61).

Additionally, the invention provides that the nucleic acids can be used to differentiate the filamentous fungi listed in general from other filamentous fungi and yeasts, such as *Candida* species. Such a determination is clinically significant, since therapies for these infections differ.

The invention further provides methods of using the nucleic acids to detect and identify the presence of the filamentous fungi listed, or particular species thereof. The method involves the steps of obtaining a sample suspected of containing filamentous fungi. The sample may be taken from an individual, such as blood, saliva, lung lavage fluids, vaginal mucosa, tissues, etc., or taken from the environment. The filamentous fungal cells can then be lysed, and the DNA extracted and precipitated. The DNA is preferably amplified using universal primers derived from the internal transcribed spacer regions, 18S, 5.8S and 28S regions of the filamentous fungal rDNA. Examples of such universal primers are shown below as ITS1 (SEQ ID NO: 62), ITS3 (SEQ ID NO: 63), ITS4 (SEQ ID NO: 64). Detection of filamentous fungal DNA is achieved by hybridizing the amplified DNA with a species-specific probe that selectively hybridizes with the DNA. Detection of hybridization is indicative of the presence of the particular genus (for generic probes) or species (for species probes) of filamentous fungus.

Preferably, detection of nucleic acid (e.g. probes or primers) hybridization can be facilitated by the use of detectable moieties. For example, the species-specific or generic probes can be labeled with digoxigenin, and an all-fungus probe, such as described in SEQ ID NO:61, can be labeled with biotin and used in a streptavidin-coated microtiter plate assay. Other detectable moieties include radioactive labeling, enzyme labeling, and fluorescent labeling, for example.

The invention further contemplates a kit containing one or more species-specific probes, which can be used for the detection of particular filamentous fungal species and genera in a sample. Such a kit can also contain the appropriate reagents for hybridizing the probe to the sample and detecting bound probe. The invention may be further demonstrated by the following non-limiting examples.

EXAMPLES

In this example, PCR assay employing universal, fungus-specific primers and a simple, rapid EIA-based format for amplicon detection were used.

Extraction of Filamentous Fungal DNA

A mechanical disruption method was used to obtain DNA from filamentous fungal species and an enzymatic disruption method described previously (13) was used to obtain DNA from yeasts. Filamentous fungi were grown for 4 to 5 days on Sabouraud dextrose agar slants (BBL, division of Becton Dickinson, Cockeysville, Md.) at 35° C. Two slants were then washed by vigorously pipeting 5 mls of 0.01 M potassium phosphate buffered saline (PBS) onto the surface of each slant and the washes were transferred to 500 ml Erlenmeyer flasks containing 250 ml of Sabouraud dextrose broth (BBL). Flasks were then incubated for 4 to 5 days on a rotary shaker (140 rpm) at ambient temperature. Growth was then harvested by vacuum filtration through a sterile Whatman #1 filter paper which had been placed into a sterile Buchner funnel attached to a 2 L side-arm flask. The resultant cellular mat was washed on the filtration apparatus three times with sterile distilled water, removed from the filter paper by gentle scraping with a rubber policeman, and placed into sterile Petri plate which was then sealed with parafilm and frozen at −20° C. until used.

Just prior to use, a portion of the frozen cellular mat, equal in size to a quarter, was removed and placed into a cold mortar (6" diameter). Liquid nitrogen was added to cover the mat which was then ground into a powder with a pestle. Additional liquid nitrogen was added as needed to keep the mat frozen during grinding.

DNA was then purified using proteinase K and RNase treatment, multiple phenol extractions, and ethanol precipitation by conventional means (26).

PCR Amplification

The fungus-specific, universal primer pair ITS3 (5'- GCA TCG ATG AAG AAC GCA GC-3') (SEQ ID NO: 63) and ITS4 (5'-TCC TCC GCT TAT TGA TAT GC-3') (SEQ ID NO: 64) was used to amplify a portion of the 5.8S rDNA region, the entire ITS2 region, and a portion of the 28S rDNA region for each species as previously described (13, 34). DNA sequencing used this primer pair and also the fungus-specific, universal primer pair ITS1 (5'-TCC GTA GGT GAA CCT GCG G-3') (SEQ ID NO: 62) and ITS4 to amplify a portion of the 18S rDNA region, the entire 5.8S region, the entire ITS1 and ITS2 regions, and a portion of the 28S rDNA region.

A DNA reagent kit (TaKaRa Biomedicals, Shiga, Japan) was used for PCR amplification of genomic DNA. PCR was performed using 2 µl of test sample in a total PCR reaction volume of 100 µl consisting of 10 µl of 10×Ex Taq buffer, 2.5 mM each of dATP, dGTP, dCTP, and dTTP, in 8 µl, 0.2 µl of each primer, and 0.5 U of TaKaRa Ex Taq DNA polymerase. Thirty cycles of amplification were performed in a Perkin-Elmer 9600 thermal cycler (Emeryville, Calif.) after initial denaturation of DNA at 95° C. for 5 minutes. Each cycle consisted of a denaturation step at 95° C. for 30 seconds, an annealing step at 58° C. for 30 seconds, and an extension step at 72° C. for 1 minute. A final extension at 72° C. for 5 minutes followed the last cycle. After amplification, samples were stored at −20° C. until used.

TABLE 1

Synthetic Universal Oligonucleotides Used in PCR and Hybridization Analyses

| Primers or Probes | Nucleotide Sequence (5' to 3') | Chemistry and Location |
|---|---|---|
| ITS3 | GCA TCG ATG AAG AAC GCA GC (SEQ ID NO:63) | 5.8S rDNA universal 5' primer |
| ITS4 | TCC TCC GCT TAT TGA TAT GC (SEQ ID NO:64) | 28S rDNA universal 3' primer |
| ITS1 | TCC GTA GGT GAA CCT GCG G (SEQ ID NO:62) | 18S rDNA universal 5' primer |

DNA Sequencing

Primary DNA amplifications were conducted as described above. The aqueous phase of the primary PCR reaction was purified using QIAquick Spin Columns (Quiagen, Chatsworth, Calif.). DNA was eluted from each column with 50 µl of heat-sterilized Tris-EDTA buffer (10 mM Tris, 1 mM EDTA, pH 8.0).

Purified DNA was labeled using a dye terminator cycle sequencing kit (ABI PRISM, Perkin Elmer, Foster City, Calif.). One mix was made for each of the primers so that sequencing could be performed in both the forward and reverse directions. The reaction volume (20 µl) contained 9.5 μl Terminator Premix, 2 μl (1 ng) DNA template, 1 μl primer (3.2 pmol) and 7.5 μl heat-sterilized distilled H$_2$O. The mixture was then placed into a pre-heated (96° C.) Perkin Elmer 9600 thermal cycler for 25 cycles of 96° C. for 10 seconds, 50° C. for 5 seconds, 60° C. for 4 minutes. The PCR product was then purified before sequencing using CentriSep spin columns (Princeton Separations, Adelphia, N.J.). DNA was then vacuum dried, resuspended in 6 μl of formamide-EDTA (5 μl deionized formamide plus 1 μl 50 mM EDTA, pH 8.0), and denatured for 2 min at 90° C. prior to sequencing using an automated capillary DNA sequencer (ABI Systems, Model 373, Bethesda, Md.).

The sequencing results were as follows:

*Aspergillus flavus* 5.8S ribosomal RNA gene, partial sequence, internal transcribed spacer 2, complete sequence, and 28S ribosomal RNA gene, partial sequence.

```
                                                (SEQ ID NO:1)
GCTGCCCATC AAGCACGGC TTGTGTGTTG GGTCGTCGTC

CCCTCTCCGG GGGGGACGGG CCCCAAAGGC AGCGGCGGCA

CCGCGTCCGA TCCTCGAGCG TATGGGGCTT TGTCACCCGC

TCTGTAGGCC CGGCCGGCGC TTGCCGAACG CAAATCAATC

TTTTTCCAGG TTGACCTCGG ATCAGGTAGG GATACCCGCT

GAACTTCAA
```

*Aspergillus fumigatus* 5.8S ribosomal RNA gene, partial sequence, internal transcribed spacer 2, complete sequence, and 28S ribosomal RNA gene, partial sequence.

```
                                                (SEQ ID NO:2)
AAACTTTCAA CAATGGATCT CTTGGTTCCG GCATCGATGA

AGAACGCAGC GAAATGCGAT AACTAATGTG AATTGCAGAA

TTCAGTGAAT CATCGAGTCT TTGAACGCAC ATTGCGCCCC

CTGGTATTCC GGGGGGCATG CCTGTCCGAG CGTCATTGCT

GCCCATCAAG CACGGCTTGT GTGTTGGGCC CCCGTCCCCC

TCTCCCGGGG GACGGGCCCG AAAGGCAGCG GCGGCACCGC

GTCCGGTCCT CGAGCGTATG GGGCTTGTCA CCTGCTCTGT

AGGCCCGGCC GGCGCCAGCC GACACCCAAC TTTATTTTTC

TAAGGTTGAC CTCGGATCAG GTAGGGATAC CCGCTGAACT TAAA
```

*Aspergillus niger* 5.8S ribosomal RNA gene, partial sequence, internal transcribed spacer 2, complete sequence, and 28S ribosomal RNA gene, partial sequence.

```
                                                (SEQ ID NO:3)
AAACTTTCAA CAATGGATCT CTTGGTTCCG GCATCGATGA

AGAACGCAGC GAAATGCGAT AACTAATGTG AATTGCAGAA

TTCAGTGAAT CATCGAGTCT TTGAACGCAC ATTGCGCCCC

CTGGTATTCC GGGGGGCATG CCTGTCCGAG CGTCATTGCT

GCCCTCAAGC ACGGCTTGTG TGTTGGGTCG CCGTCCCCCT

CTCCGGGGG ACGGGCCCGA AAGGCAGCGG CGGCACCGCG

TCCGATCCTC GAGCGTATGG GGCTTTGTCA CCTGCTCTGT

AGGCCCGGCC GGCGCCTGCC GACGTTATCC AACCATTTTT

TTCCAGGTTG ACCTCGGATC AGGTAGGGAT ACCCGCTGAA CTTAA
```

*Aspergillus terreus* 5.8S ribosomal RNA gene, partial sequence, internal transcribed spacer 2, complete sequence, and 28S ribosomal RNA gene, partial sequence.

```
                                                (SEQ ID NO:4)
AAACTTTCAA CAATGGATCT CTTGGTTCCG GCATCGATGA

AGAACGCAGC GAAATGCGAT AACTAATGTG AATTGCAGAA

TTCAGTGAAT CATCGAGTCT TTGAACGCAC ATTGCGCCCC

CTGGTATTCC GGGGGGGCAT GCCTGTCCGA GCGTCATTGC

TGCCCTCAAG CCCGGCTTGT GTGTTGGGCC CTCGTCCCCC

GGCTCCCGGG GGACGGGCCC GAAAGGCACC GGCGGCACCG

CGTCCGGTCC TCGAGCGTAT GGGGCTTCGT CTTCCGCTCC

GTAGGCCCGG CCGGCGCCCG CCGAACGCAT TTATTTGCAA

CTTGTTTTTT TTTCCAGGTT GACCTCGGAT CAGGT
```

*Aspergillus nidulans* 5.8S ribosomal RNA gene, partial sequence, internal transcribed spacer 2, complete sequence, and 28S ribosomal RNA gene, partial sequence.

```
                                                (SEQ ID NO:5)
AAACTTTCAA CAATGGATCT CTTGGTTCCG GCATCGATGA

AGAACGCAGC GAACTGCGAT AAGTAATGTG AATTGCAGAA

TTCAGTGAAT CATCGAGTCT TTGAACGCAC ATTGCGCCCC

CTGGCATTCC GGGGGGCATG CCTGTCCGAG CGTCATTGCT

GCCCTCAAGC CCGGCTTGTG TGTTGGGTCG TCGTCCCCCC

CCCCGGGGGA CGGGCCCGAA AGGCAGCGGC GGCACCGGTC

CGGTCCTCGA GCGTATGGGG CTTGGTCACC CGCTCGATTA

GGGCCGGCCG GGCGCCAGCC GGCGTCTCCA ACCTTATCTT

TCTCAGGTTG ACCTCGGATC AGGTAGGGAT ACCCGCTGAA CTTAA
```

*Fusarium solani* (strain ATCC62877) internal transcribed spacer 2 and adjacent regions.

```
                                                (SEQ ID NO:6)
GAAAATGCGA TAAGTAATGT GAATTGCAGA ATTCAGTGAA

TCATCGAATC TTTGAACGCA CATTGCGCCC GCCAGTATTC

TGGCGGGCAT GCCTGTTCGA GCGTCATTAC AACCCTCAGG

CCCCCGGGCC TGGCGTTGGG GATCGGCGGA AGCCCCCTGC

GGGCACAACG CCGTCCCCCA AATACAGTGG CGGTCCCGCC

GCAGCTTCCA TTGCGTAGTA GCTAACACCT CGCAACTGGA

GAGCGGCGCG GCCACGCCGT AAAACACCCA ACTTCTGAAT

GTTGACCTCG AATCAGGTAG GAATACCCGC TGAACTTAA
```

*Fusarium moniliforme* (strain ATCC38519) internal transcribed spacer 2 and adjacent regions.

```
                                    (SEQ ID NO:7)
AAATGCGATA AGTAATGTGA ATTGCAAAAT TCAGTGAATC

ATCGAATCTT TGAACGCACA TTGCGCCCGC CAGTATTCTG

GCGGGCATGC CTGTTCGAGC GTCATTTCAA CCCTCAAGCC

CCCGGGTTTG GTGTTGGGGA TCGGCAAGCC CTTGCGGCAA

GCCGGCCCCG AAATCTAGTG GCGGTCTCGC TGCAGCTTCC

ATTGCGTAGT AGTAAAACCC TCGCAACTGG TACGCGGCGC

GGCCAAGCCG TTAAACCCCC AACTTCTGAA TGTTGACCTC

GGATCAGGTA GGAATACCCG CTGAACTTAA
```

*Mucor rouxii* (strain ATCC24905) internal transcribed spacer 2 and adjacent regions.

```
                                    (SEQ ID NO:8)
AAAGTGCGAT AACTAGTGTG AATTGCATAT TCAGTGAATC

ATCGAGTCTT TGAACGCAAC TTGCGCTCAT TGGTATTCCA

ATGAGCACGC CTGTTTCAGT ATCAAAACAA ACCCTCTATC

CAGCATTTTG TTGAATAGGA ATACTGAGAG TCTCTTGATC

TATTCTGATC TCGAACCTCT TGAAATGTAC AAAGGCCTGA

TCTTGTTTAA ATGCCTGAAC TTTTTTTTAA TATAAAGAGA

AGCTCTTGCG GTAAACTGTG CTGGGCCTC CCAAATAATA

CTCTTTTTAA ATTTGATCTG AAATCAGGCG GGATTACCCG

CTGAACTTAA
```

*Mucor racemosus* (strain ATCC22365) internal transcribed spacer 2 and adjacent regions.

```
                                    (SEQ ID NO:9)
AAAGTGCGAT AACTAGTGTG AATTGCATAT TCAGTGAATC

ATCGAGTCTT TGAACGCAAC TTGCGCTCAT TGGTATTCCA

ATGAGCACGC CTGTTTCAGT ATCAAAACAA ACCCTCTATC

CAACTTTTGT TGTATAGGAT TATTGGGGGC CTCTCGATCT

GTATAGATCT TGAAATCCCT GAAATTTACT AAGGCCTGAA

CTTGTTTAAA TGCCTGAACT TTTTTTTAAT ATAAAGGAAA

GCTCTTGTAA TTGACTTTGA TGGGGCCTCC CAAATAAATC

TCTTTTAAAT TTGATCTGAA ATCAGGCGGG ATTACCCGCT

GAACTTAA
```

*Mucor plumbeus* (strain ATCC4740) internal transcribed spacer 2 and adjacent regions.

```
                                    (SEQ ID NO:10)
AAAGTGCGAT AACTAGTGTG AATTGCATAT TCAGTGAATC

ATCGAGTCTT TGAACGCAAC TTGCGCTCAT TGGTATTCCA

ATGAGCACGC CTGTTTCAGT ATCAAAACAA ACCCTCTATC

CAACTTTTGT TGTATAGGAT TATTGGGGGC CTCTCGATCT

GTATAGATCT TGAAACCCTT GAAATTTACT AAGGCCTGAA

CTTGTTTAAT GCCTGAACTT TTTTTTAATA TAAAGGAAAG

CTCTTGTAAT TGACTTTGAT GGGGCCTCCC AAATAAATCT

TTTTTAAATT TGATCTGAAA TCAGGTGGGA TTACCCGCTG

AACTTAA
```

*Mucor indicus* (strain ATCC4857) internal transcribed spacer 2 and adjacent regions.

```
                                    (SEQ ID NO:11)
AAAGTGCGAT AACTAGTGTG AATTGCATAT TCAGTGAATC

ATCGAGTCTT TGAACGCATC TTGCACTCAA TGGTATTCCA

TTGAGTACGC CTGTTTCAGT ATCAAAAAC AACCCTTATT

CAAAATTCTT TTTTTGAATA GATATGAGTG TAGCAACCTT

ACAAGTTGAG ACATTTTAAA TAAAGTCAGG CCATATCGTG

GATTGAGTGC CGATACTTTT TTAATTTTGA AAAGGTAAAG

CATGTTGATG TCCGCTTTTT GGGCCTCCCA AATAACTTTT

TAAACTTGAT CTGAAATCAG GTGGGATTAC CCGCTGAACT

TAA
```

*Mucor circinelloides f. circinelloides* (strain ATCC1209B) internal transcribed spacer 2 and adjacent regions.

```
                                    (SEQ ID NO:12)
AAAGTGCGAT AACTAGTGTG AATTGCATAT TCAGTGAATC

ATCGAGTCTT TGAACGCAAC TTGCGCTCAT TGGTATTCCA

ATGAGCACGC CTGTTTCAGT ATCAAAACAA ACCCTCTATC

CAACATTTTT GTTGAATAGG ATGACTGAGA GTCTCTTGAT

CTATTCTGAT CTCGAAGCTC TTGAAATGTA CAAAGGCCTG

ATCTTGTTTG AATGCCTGAA CTTTTTTTTA ATATAAAGAG

AAGCTCTTGC GGTAAACTGT GCTGGGCCT CCCAAATAAC

ACATCTTTAA ATTTGATCTG AAATCAGGT GGGACTACCC

GCTGAACTT AA
```

*Rhizopus oryzae* (strain ATCC34965) internal transcribed spacer 2 and adjacent regions.

```
                                    (SEQ ID NO:13)
AGTGCGATAA CTAGTGTGAA TTGCATATTC AGTGAATCAT

CGAGTCTTTG AACGCAGCTT GCACTCTATG GTTTTTCTAT

AGAGTACGCC TGCTTCAGTA TCATCACAAA CCCACACATA

ACATTTGTTT ATGTGGTGAT GGGTCGCATC GCTGTTTTAT

TACAGTGAGC ACCTAAAATG TGTGTGATTT TCTGTCTGGC

TTGCTAGGCA GGAATATTAC GCTGGTCTCA GGATCTTTTT

TTTTGGTTCG CCCAGGAAGT AAAGTACAAG AGTATAATCC
```

-continued

AGTAACTTTC AAACTATGAT CTGAAGTCAG GTGGGATTAC

CCGCTGAACT TAA

*Rhizopus oryzae* (strain ATCC11886) internal transcribed spacer 2 and adjacent regions.

(SEQ ID NO:14)
AGTGCGATAA CTAGTGTGAA TTGCATATTC AGTGAATCAT

CGAGTCTTTG AACGCAGCTT GCACTCTATG GTTTTTCTAT

AGAGTACGCC TGCTTCAGTA TCATCACAAA CCCACACATA

ACATTTGTTT ATGTGGTAAT GGGTCGCATC GCTGTTTTAT

TACAGTGAGC ACCTAAAATG TGTGTGATTT TCTGTCTGGC

TTGCTAGGCA GGAATATTAC GCTGGTCTCA GGATCTTTTT

CTTTGGTTCG CCCAGGAAGT AAAGTACAAG AGTATAATCC

AGCAACTTTC AAACTATGAT CTGAAGTCAG GTGGGATTAC

CCGCTGAACT TAA

*Rhizopus microsporus* (strain ATCC14056) internal transcribed spacer 2 and adjacent regions.

(SEQ ID NO:15)
AAAGTGCGAT AACTAGTGTG AATTGCATAT TCGTGAATCA

TCGAGTCTTT GAACGCAGCT TGCACTCTAT GGATCTTCTA

TAGAGTACGC TTGCTTCAGT ATCATAACCA ACCCACACAT

AAAATTTATT TTATGTGGTG ATGGACAAGC TCGGTTAAAT

TTAATTATTA TACCGATTGT CTAAAATACA GCCTCTTTGT

AATTTTCATT AAATTACGAA CTACCTAGCC ATCGTGCTTT

TTTGGTCCAA CCAAAAAACA TATAATCTAG GGGTTCTGCT

AGCCAGCAGA TATTTTAATG ATCTTTAACT ATGATCTGAA

GTCAAGTGGG ACTACCCGCT GAACTTAA

*Rhizopus microsporus* (strain ATCC12276) internal transcribed spacer 2 and adjacent regions.

(SEQ ID NO:16)
AAAGTGCGAT AACTAGTGTG AATTGCATAT TCGTGAATCA

TCGAGTCTTT GAACGCAGCT TGCACTCTAT GGATCTTCTA

TAGAGTACGC TTGCTTCAGT ATCATAACCA ACCCACACAT

AAAATTTATT TTATGTGGTG ATGGACAAGC TCGGTTAAAT

TTAATTATTA TACCGATTGT CTAAAATACA GCCTCTTTGT

AATTTTCATT AAATTACGAA CTACCTAGCC ATCGTGCTTT

TTTGGTCCAA CCAAAAAACA TATAATCTAG GGGTTCTGCT

AGCCAGCAAA TATTTTAATG ATCTTTAACC TATGATCTGA

AGTCAAGTGG GACTACCCGC TGAACTTAA

*Rhizopus circinans* (strain ATCC34106) internal transcribed spacer 2 and adjacent regions.

(SEQ ID NO:17)
AAATTGCGAT AACTAGTGTG AATTGCATTT TCAGTGAATC

ATCGAGTCTT TGAACGCAT CTTGCGCTCT TGGGATTCTT

CCCTAGAGCA CACTTGCTTC AGTATCATAA CAAAACCCTC

ACCTAATATT TTTTTTTTTT AAAAAAAAAA TATTAGAGTG

GTATTGGGGT CTCTTTGGTA ATTCTTTGTA ATTATAAAAG

TACCCTTAAA TGTCATAAAC AGGTTAGCTT TAGCTTGCCT

TTAAAGATCT TCTTAGGGTA TCATTACTTT TCGTAAATCT

TTAATAGGCC TGTCACATAA TTCTACCCTT AAATTTCTTA

AACCTTGATC TGAAGTCAAG TGGGAGTACC CGCTGAACTT AA

*Rhizopus circinans* (strain ATCC34101) internal transcribed spacer 2 and adjacent regions.

(SEQ ID NO:18)
AAATTGCGAT AACTAGTGTG AATTGCATTT TCAGTGAATC

ATCGAGTCTT TGAACGCATC TTGCGCTCTT GGGATTCTTC

CCTAGAGCAC ACTTGCTTCA GTATCATAAC AAAACCCTCA

CCTAATATTT TTTTTAAAA AAAAAAATA TTAGAGTGGT

ATTGGGGTCT CTTTGGTAAT TCTTTGTAAT TATAAAAGTA

CCCTTAAATG TCATAAACAG GTTAGCTTTA GCTTGCCTTT

AAAGATCTTC TTAGGGTATC ATTACTTTC GTAAATCTTT

AATAGGCCTG TCACATAATT CTACCCTTAA ATTTCTTAAA

CCTTGATCTG AAGTCAAGTG GGAGTACCCG CTGAACTTAA

*Rhizous stolonifer* (strains ATCC14037 and 6227A) internal transcribed spacer 2 and adjacent regions.

(SEQ ID NO:19)
AAAGTGCGAT AACTAGTGTG AATTGCATAT TCAGTGAATC

ATCGAGTCTT TGAACGCAAC TTGCACTCTA TGGTTTTCCG

TAAAGTACGC TTGCTTCAGT ATCATAAAGA CCCCATCCTG

ATTATTATTT TTTTATTAAA ATAATTAATT TTGGAGATAA

TAAAAATGAG GCTCTTTCTT TTCTTTTTTT TTTTTTTAAA

AAAAAGGGGG GGAAAGGGTC TTTTAAAATG GGCAAATTCT

GGGTTTTTA CTAAACCTGA ACTCCCCCCA AAAATTCAAA

AAAAAAAAAA TGGGTTTTAC CAAATTTTTT TTTTTTTTCT

CCTTTTTGTG TAGTTAATAC TCTATTAAAT TTATTTACTT

GGTATTATAA CGATTATGCA AGAAGGGAGA GAACAAAGAA

TAATGAAAGA GAGTTTTTAA ATAAATTCTT TTTTCATTTT

TTCAATCAAT GATCTGAAGT CAAGTGGGAT TACCCGCTGA

ACTTAA

*Rhizomucor pusillus* (strain ATCC36606) internal transcribed spacer 2 and adjacent regions.

(SEQ ID NO:20)
AAATTGCGAA AAGTAATGCG ATCTGCAGCC TTTGCGAATC

ATCGAATTCT CGAACGCACC TTGCACCCTT TGGTTCATCC

ATTGGGTACG TCTAGTTCAG TATCTTTATT AACCCCTAAA

GGTTTATTTT TTGATAAATC TTTGGATTTG CGGTGCTGAT

GGATTTTCAT CCGTTCAAGC TACCCGAACA ATTTGTATGT

TGTTGACCCT TGATATTTCC TTGAGGGCTT GCATTGGTAT

CTAATTTTTT ACCAGTGTGC TTCGAGATGA TCAAGTATAA

AGGTCAATCA ACCACAAATA AATTTCAACT ATGGATCTGA

ACTTAGATGG GATTACCCGC TGAACTTAA

*Absidia corymbifera* (strain ATCC46774) internal transcribed spacer 2 and adjacent regions.

(SEQ ID NO:21)
AAAGTGCGAT AATTATTGCG ACTTGCATTC ATAGCGAATC

ATCGAGTTCT CGAACGCATC TTGCGCCTAG TAGTCAATCT

ACTAGGCACA GTTGTTTCAG TATCTGCAAC TACCAATCAG

TTCAACTTGG TTCTTTGAAC CTAAGCGAGC TGGAAATGGG

CTTGTGTTGA TGGCATTCAG TTGCTGTCAT GGCCTTAAAT

ACATTTAGTC CTAGGCAATT GGCTTTAGTC ATTTGCCGGA

TGTAGACTCT AGAGTGCCTG AGGAGCAACG ACTTGGTTAG

TGAGTTCATA ATTCCAAGTC AATCAGTCTC TTCTTGAACT

AGGTCTTAAT CTTTATGGAC TAGTGAGAGG ATCTAACTTG

GGTCTTCTCT TAAAACAAAC TCACATCTAG ATCTGAAATC

AACTGAGATC ACCCGCTGAA CTTAA

*Absidia corymbifera* (strain ATCC46773) internal transcribed spacer 2 and adjacent regions.

(SEQ ID NO:22)
AAAGTGCGAT AATTATTGCG ACTTGCATTC ATAGTGAATC

ATCGAGTTCT TGAACGCATC TTGCGCCTAG TAGTCAATCT

ACTAGGCACA GTTGTTTCAG TATCTGCATC CACCAATCAA

CTTAACCTTT TGTGTTGAGT TGGAACTGGG CTTCTAGTTG

ATGGCATTTA GTTGCTGTCA TGGCCTTAAA TCAATGTCCT

AGGTGTTAGA ACATCTAACA CCGGATGGAA ACTTTAGAGC

GCTTTAAGAG CAGCTTGGTT AGTGAGTTCA ATAATTCCAA

GCATTAAGTC TTTTAATGAA CTAGCTTTTC TATCTATGGG

ACACTACTTG GAGAAATCCA AGTAACCTTT AAACTCCCAT

TTAGATCTGA AATCAACTGA GACCACCCGC TGAACTTAA

*Cunninghamella elegans* (strain ATCC42113) internal transcribed spacer 2 and adjacent regions.

(SEQ ID NO:23)
AAATCGCGAT ATGTAATGTG ACTGCCTATA GTGAATCATC

AAATCTTTGA AACGCATCTT GCACCTTATG GTATTCCATA

AGGTACGTCT GTTTCAGTAC CACTAATAAA TCTCTCTCTA

TCCTTGATGA TAGAAAAAAA AAAAATAATT TTTACTGGGC

CCGGGGAATC CTTTTTTTTT TTTAATAAAA AGGACCAATT

TTGGCCCAAA AAAAAGGGTT GAACTTTTTT TACCAGATCT

TGCATCTAGT AAAAACCTAG TCGGCTTTAA TAGATTTTTA

TTTTCTATTA AGTTTATAGC CATTCTTATA TTTTTTAAAA

TCTTGGCCTG AAATCAGATG GGATACCCGC TGAACTTAA

*Pseudallescheria boydii* (strain ATCC44328) internal transcribed spacer 2 and adjacent regions (teleomorph of *Scedosporium apiospermum*).

(SEQ ID NO:24)
AAATGCGATA AGTAATGTAA ATTGCAAAAT TCAGTGAATC

ATCGAATCTT TGAAACGCAC ATTGCGCCCG GCAGTAATCT

GCCGGGCATG CCTGTCCGAG CGTCATTTCA ACCCTCGAAC

CTCCGTTTC CTTAGGGAAG CCTAGGGTCG GTGTTGGGGC

GCTACGGCAA GTCCTCGCAA CCCCCGTAGG CCCTGAAATA

CAGTGGCGGT CCCGCCGCGG TTGCCTTCTG CGTAGTAAGT

CTCTTTTGCA AGCTCGCATT GGGTCCCGGC GGAGGCCTGC

CGTCAAACCA CCTAACAACT CCAGATGGTT TGACCTCGGA

TCAGGTAGGG TTACCCGCTG AACTTAA

*Pseudallescheria boydii* (strain ATCC36282) internal transcribed spacer 2 and adjacent regions (teleomorph of *Scedosporium apiospermum*).

(SEQ ID NO:25)
GAAATGCGAT AAGTAATGTG AATTGCAGAA TTCAGTGAAT

CATCGAATCT TTGAAACGCA CATTGCGCCC GGCAGTAATC

TGCCGGGCAT GCCTGTCCGA GCGTCATTTC AACCCTCGAA

CCTCCGTTTC CTCAGGGAAG CTCAGGGTCG GTGTTGGGGC

GCTACGGCAA GTCTTCGCAA CCCTCCGTAG GCCCTGAAAT

ACAGTGGCGG TCCCGCCGCG GTTGCCTTCT GCGTAGAAGT

CTCTTTTGCA AGCTCGCATT GGGTCCCGGC GGAGGCCTGC

CGTCAAACCA CCTATAACTC CAAATGGTTT GACCTCGGAT

CAGGTAGGGT TACCCGCTGA ACTTAA

*Scedosporium apiospermum* (strain ATCC64215) internal transcribed spacer 2 and adjacent regions.

(SEQ ID NO:26)
GAAATGCGAT AAGTAATGTG AATTGCAGAA TTCAGTGAATC

ATCGAATCTT TGAACGCACA TTGCGCCCGG CAGTAATCTG

-continued

```
CCGGGCATGC CTGTCCGAGC GTCATTTCAA CCCTCGAACC

TCCGTTTCCT CAGGGAAGCT CAGGGTCGGT GTTGGGGCGC

TACGGCGAGT CTTCGCGACC CTCCGTAGGC CCTGAAATAC

AGTGGCGGTC CCGCCGCGGT TGCCTTCTGC GTAGTAAGTC

TCTTTTGCAA GCTCGCATTG GGTCCCGGCG GAGGCCTGCC

GTCAAACCAC CTATAACTCC AGATGGTTTG ACCTCGGATC

AGGTAGGTAC CCGCTGAACT TAA
```

*Scedosporium apiospermum* (strain ATCC46173) internal transcribed spacer 2 and adjacent regions.

```
                                        (SEQ ID NO:27)
AAATGCGATA AGTAATGTGA ATTGCAGAAT TCAGTGAATC

ATCGAATCTT TGAACGCACA TTGCGCCCGG CAGTAATCTG

CCGGGCATGC CTGTCCGAGC GTCATTTCAA CCCTCGAACC

TCCGTTTCCT CAGGGAAGCT CAGGGTCGGT GTTGGGGCGC

TACGGCGAGT CTTCGCGACC CTCCGTAGGC CCTGAAATAC

AGTGGCGGTC CCGCCGCGGT TGCCTTCTGC GTAGTAAGTC

TCTTTTGCAA GCTCGCATTG GGTCCCGGCG GAGGCCTGCC

GTCAAACCAC CTATAACTCC AGATGGTTTG ACCTCGGATC

AGGTAGGTAC CCGCTGAACT TAA
```

*Penicillium notatum* (strain ATCC10108) internal transcribed spacer 2 and adjacent regions.

```
                                        (SEQ ID NO:28)
AAATGCGATA CGTAATGTGA ATTGCAAATT CAGTGAATCA

TCGAGTCTT TGAACGCACA TTGCGCCCCC TGGTATTCCG

GGGGGCATGC CTGTCCGAGC GTCATTGCTG CCCTCAAGCA

CGGCTTGTGT GTTGGGCCCC GTCCTCCGAT CCCGGGGGAC

GGGCCCGAAA GGCAGCGGCG GCACCGCGTC CGGTCCTCGA

GCGTATGGGG CTTTGTCACC CGCTCTGTAG GCCCGGCCGG

CGCTTGCCGA TCAACCCAAA TTTTTATCCA GGTTGACCTC

GGATCAGGTA GGGATACCCG CTGAACTTAA
```

*Sporothrix schenckii* (strain ATCC14284) internal transcribed spacer 2 and adjacent regions.

```
                                        (SEQ ID NO:29)
GAAATGCGAT ACTAATGTGA ATTGCAGAAT TCAGCGAACC

ATCGAATCTT TGAACGCACA TTGCGCCCGC CAGCATTCTG

GCGGGCATGC CTGTCCGAGC GTCATTTCCC CCTCACGCG

CCCCGTTGCG CGCTGGTGTT GGGGCGCCCT CCGCCTGGCG

GGGGGCCCCC GAAAGCGAGT GGCGGGCCCT GTGGAAGGCT

CCGAGCGCAG TACCGAACGC ATGTTCTCCC CTCGCTCCGG

AGGCCCCCCA GGCGCCCTGC CGGTGAAAAC GCGCATGACG

CGCAGCTCTT TTTACAAGGT TGACCTCGGA TCAGGTGAGG

ATACCCGCTG ACTTAA
```

Contamination Precautions

Precautions were taken to avoid possible contamination of PCR samples by following the guidelines of Fujita and Kwok (13, 22). All buffers and distilled water used for PCR assays were autoclaved and fresh PCR reagents were aliquoted prior to use. Physical separation of laboratory areas used to prepare PCR assays and to analyze PCR products, and the use of aerosol-resistant pipette tips, reduced possible cross-contamination of samples by aerosols. Appropriate negative controls were included in each test run, including controls omitting either the primer or the DNA template during PCR assays.

Agarose Gel Electrophoresis

Gel electrophoresis was conducted in TBE buffer (0.1 M Tris, 0.09 M boric acid, 1 mM EDTA, pH 8.4) at 80 V for 1 to 2 hours using gels composed of 1% (w/vol) agarose (International Technologies, New Haven, Conn.) and 1% (w/vol) NuSieve agar (FMC Bioproducts, Rockland, Me.). Gels were stained with 0.5 µg of ethidium bromide (EtBr) per ml of distilled $H_2O$ for 10 minutes followed by three serial washes for 10 minutes each with distilled $H_2O$.

Microtitration Plate Enzyme Immunoassay for the Detection of PCR Products

Amplicons were detected using species-specific and genus probes labeled with digoxigenin andan all-filamentous fungal probe labeled with biotin in a streptavidin-coated microtiter plate format (13, 34). Ten µl of PCR product was added to each 1.5 ml Eppendorf tube. Single-stranded DNA was then prepared by heating the tubes at 95° C. for 5 minutes and cooling immediately on ice. Two-tenths of a ml of hybridization solution [4×SSC (saline sodium citrate buffer, 0.6 M NaCl, 0.06 M trisodium citrate, pH 7.0) containing 20 mM Hepes, 2 mM EDTA, and 0.15% (vol/vol) Tween 20] supplemented with 50 ng/ml each of the all-*Aspergillus* biotinylated probe and a species-specific digoxigenin-labeled probe was added to each tube containing denatured PCR product. Tubes were mixed by inversion and placed in a water bath at 37° C. to allow probes to anneal to PCR product DNA. After 1 hour, 100 µl of each sample was added to duplicate wells of a commercially prepared streptavidin-coated microtitration plate (Boehringer Mannheim, Indianapolis, Ind.). The plate was incubated at ambient temperature for 1 hour with shaking, using a microtitration plate shaker (manufactured for Dynatech by CLTI, Middletown, N.Y.). Plates were washed 6 times with 0.01 M potassium phosphate buffered saline, pH 7.2, containing 0.05% Tween 20 (PBST). Each well then received 100 µl of horseradish peroxidase-conjugated, anti-digoxigenin Fab fragment (Boehringer Mannheim) diluted 1:1000 in hybridization buffer. After incubation at ambient temperature for 30 minutes with shaking, the plate was washed 6 times with PBST. One hundred µl of a mixture of one volume of 3, 3', 5, 5'-tetramethyl benzidine peroxidase substrate (Kirkegaard and Perry Laboratories, Inc., Gaithersberg, Md.) and one volume of peroxidase solution (Kirkegaard and Perry Laboratories) was added to each well and the plate was placed at ambient temperature for 10 minutes for color development. The $A_{650nm}$ of each well was determined with a microtitration plate reader (UV Max, Molecular Devices, Inc., Menlo Park, Calif.). The absorbance value for the reagent blank, where DNA was absent but replaced with distilled $H_2O$, was subtracted from each test sample.

Statistical Analysis

The Student's t test was used to determine differences between sample means. Means are expressed as the mean plus or minus the standard error from the mean. Differences were considered significant when P<0.05.

The following probes were used to detect and distinguish each species.

TABLE 2

Probe Sequences

| PROBES | 5' to 3' OLIGONUCLEOTIDE SEQUENCE | |
|---|---|---|
| Generic Biotin Probe | 5' end-labeled biotinylated probe 5.8S region of rDNA | |
| B-58 | GAA TCA TCG A(AG)T CTT TGA ACG | SEQ ID NO 61 |
| Digoxigenin-probe | 5' end-labeled digoxigenin probe ITS2 region of rDNA | |
| Aspergillus species | | |
| A. flavus 22 | GCA AAT CAA TCT TTT TCC | SEQ ID NO 30 |
| A. flavus 23 | GAA CGC AAA TCA ATC TTT | SEQ ID NO 31 |
| A. fumigatus | CCG ACA CCC ATC TTT ATT | SEQ ID NO 32 |
| A. niger | GAC GTT ATC CAA CCA TTT | SEQ ID NO 33 |
| A. nidulans | GGC GTC TCC AAC CTT ATC | SEQ ID NO 35 |
| A. terreus | GCA TTT ATT TGC AAC TTG | SEQ ID NO 34 |
| Fusarium species | | |
| F. moniliforme | TCT AGT GAC GGT CTC GCT | SEQ ID NO 49 |
| F. oxysporum | CGT TAA TTC GCG TTC CTC | SEQ ID NO 50 |
| F. solani | CTA ACA CCT CGC AAC TGG AGA | SEQ ID NO 51 |
| Mucor species | | |
| M. circinelloides | AAC ATT TTT GTG AAT AGG ATG | SEQ ID NO 39 |
| M. indicus | CGT GGA TTG AGT GCC GAT | SEQ ID NO 38 |
| M. plumbeus | GAA ACC CTT GAA ATT | SEQ ID NO 37 |
| M. rouxii | GAA TAG GAA TAC TGA GAG | SEQ ID NO 36 |
| M. racemosus | GAA ATC CCT GAA ATT | SEQ ID NO 40 |
| Penicillium species | | |
| Penicillium marneffei 1 | GGG TTG GTC ACC ACC ATA | SEQ ID NO 47 |
| Penicillium marneffei 2 | TGG TCA CCA CCA TAT TTA | SEQ ID NO 48 |
| Penicillium notatum | GAT CAA CCC AAA TTT TTA | SEQ ID NO 46 |
| Rhizopus species | | |
| R. circinans | CTT AGG GTA TCA TTA CTT | SEQ ID NO 42 |
| R. microsporus | CAT ATA ATC TAG GGG TTC | SEQ ID NO 57 |
| R. oryzae | GAG TAT AAT CCA G(CT)A ACT | SEQ ID NO 41 |
| R. stolonifer | CTT GGT ATT ATA ACG ATT | SEQ ID NO 44 |
| Rhizomucor pusillus | TCC TTG AGG GCT TGC ATT | SEQ ID NO 43 |
| Other Genera | | |
| Absidia corymbifera | GTT GCT GTC ATG GCC TTA | SEQ ID NO 55 |
| Cunninghamella elegans 4 | TAG TCG GCT TTA ATA GAT | SEQ ID NO 52 |
| Cunninghamella elegans 5 | TAT TAA GTT TAT AGC CAT | SEQ ID NO 53 |
| Cunninghamella elegans 6 | TAA GTT TAT AGC CAT TCT | SEQ ID NO 54 |
| Pseudallescheria boydii | AAG TCT CTT TTG CAA GCT | SEQ ID NO 45 |
| Sporothrix schoenckii | GAC GCG CAG CTC TTT TTA | SEQ ID NO 56 |
| Genus Probes | | |
| G-ASPERGILLUS | CCT CGA GCG TAT GGG GCT | SEQ ID NO 58 |
| G-FUSARIUM | CCC AAC TTC TGA ATG TTG | SEQ ID NO 59 |
| G-MUCOR | (AC)TG GGG CCT CCC AAA TAA | SEQ ID NO 60 |

Species-specific probes to the ITS2 region of rDNA for *Aspergillus fumigatus* (SEQ ID NO:32), *A. flavus* (SEQ ID NO:31), *A. niger* SEQ ID NO:33), *A. terreus* (SEQ ID NO:34), and *A. nidulans* (SEQ ID NO:35) correctly identified each of the respective species (P<0.001), and gave no false-positive reactions with *Rhizopus, Mucor, Fusarium, Penicillium*, or *Candida* species. The *A. flavus* probe also recognized *A. oryzae*, which belongs to the *A. flavus* group. Identification time was reduced from a mean of 5 days by conventional methods to 8 hours.

TABLE 3

Aspergillus Probes

| Fungus | A. fumigatus | A. nidulans | A. niger | A. terreus | A. flavus |
|---|---|---|---|---|---|
| A. fumigatus (n = 6) | 2.197 ± 0.187 | 0.002 | 0.000 | 0.001 | 0.001 |
| A. nidulans (n = 3) | 0.001 | 1.315 ± 0.464 | 0.002 | 0.000 | 0.001 |
| A. niger (n = 5) | 0.000 | 0.000 | 1.242 ± 0.471 | 0.001 | 0.003 |
| A. terreus (n = 4) | 0.001 | 0.000 | 0.001 | 1.603 ± 0.378 | 0.001 |
| A. flavus (n = 6) | 0.001 | 0.001 | 0.000 | 0.001 | 2.043 ± 0.390 |
| A. oryzae (n = 2) | 0.001 | 0.002 | 0.001 | 0.001 | 2.445 ± 0.106 |
| A. parasitica (n = 1) | 0.001 | 0.002 | 0.002 | 0.002 | 0.051 |
| A. clavus (n = 1) | 0.005 | 0.005 | 0.006 | 0.005 | 0.003 |
| C. albicans (n = 1) | 0.002 | 0.001 | 0.002 | 0.000 | 0.000 |
| C. parasilosis (n = 1) | 0.001 | 0.002 | 0.002 | 0.002 | 0.001 |
| C. glabrata (n = 1) | 0.001 | 0.003 | 0.001 | 0.001 | 0.005 |
| C. krusei (n = 1) | 0.002 | 0.002 | 0.002 | 0.001 | 0.001 |
| C. tropicalis (n = 1) | 0.002 | 0.002 | 0.001 | 0.000 | 0.001 |
| F. moniliforme (n = 1) | 0.003 | 0.003 | 0.001 | 0.001 | 0.001 |
| F. solani (n = 1) | 0.006 | 0.002 | 0.001 | 0.000 | 0.001 |
| R. oryzae (n = 1) | 0.001 | 0.001 | 0.001 | 0.001 | 0.001 |
| M. racemosus (n = 1) | 0.001 | 0.002 | 0.005 | 0.002 | 0.000 |
| P. notatum (n = 1) | 0.001 | 0.002 | 0.002 | 0.002 | 0.000 |
| Avg ± SD negative controls | 0.001 ± 0.002 | 0.001 ± 0.001 | 0.000 ± 0.002 | 0.000 ± 0.002 | 0.002 ± 0.010 |

Species-specific probes to the ITS2 region of rDNA for *Fusarium oxysporum, F. solani*, and *F. moniliforme*, correctly identified each of the respective species (P<0.001), and gave no false-positive reactions with *Blastomyces, Apophysomyces, Candida, Aspergillus, Mucor, Penecillium, Rhizopus, Rhizomucor, Absidia, Cunninghamella, Pseudallescheria, Sporothrix*, or *Neosartorya*. Empty boxes in Table 4 represent zero probe reactivity.

TABLE 4

Fusarium Probes

| Fungus | F. oxysporum | F. solani | F. moniliforme | Generic Fusarium |
|---|---|---|---|---|
| F. oxysporum (n = 3) | 1.40 ± 0.13 | | | 1.76 ± 0.27 |
| F. solani (n = 5) | | 1.57 ± 0.07 | | 1.35 ± 0.28 |
| F. moniliforme (n = 2) | | | 1.40 ± 0.01 | 1.34 ± 0.91 |

TABLE 4-continued

Fusarium Probes

| Fungus | F. oxysporum | F. solani | F. moniliforme | Generic Fusarium |
|---|---|---|---|---|
| Negative control | | | | |
| A. fumigatus | | | | |
| A. flavus | | | | |
| A. niger | | | | |
| A. nidulans | | | | |
| A. terreus | | | | |
| A. parasiticus | | | | |
| A. clavatus | | | | |
| P. marneffei | | 0.01 | 0.01 | |
| P. notatum | 0.01 | 0.01 | 0.01 | |
| Rhizopus oryzae | | 0.03 | 0.01 | |
| Rhizopus microsporus | | 0.01 | 0.01 | |
| Rhizopus circinans | | 0.01 | 0.01 | |
| Rhizopus stolonifer | | 0.01 | 0.01 | |
| Rhizomucor pusillus | | 0.03 | 0.02 | |
| M. racemosus | | | | |
| M. circinelloides | | | | |
| M. rouxii | | | | |
| M. plumbeus | | | | |
| M. indicus | | | | |
| Absidia corymbifera | | 0.01 | 0.01 | |
| Cunninghamella elegans | | 0.01 | 0.02 | |
| P. boydii | | | 0.02 | |
| Sporothrix schenckii | | 0.01 | 0.01 | |
| C. albicans | | | | |
| C. tropicalis | | | | |
| C. krusei | | | | |
| C. parasilosis | | | | |
| C. glabrata | | | | |
| Neosartorya fischeri | | | 0.01 | |
| Blastomyces dermatitidis | | | | |
| Apophysomyces elegans | | | | |
| Average of negative controls | 0.001 ± 0.002 | 0.005 ± 0.01 | 0.004 ± 0.006 | |

Species-specific probes to various other zygomyces are presented in Table 5, showing correct identification of each species and no false positives. The exceptions are that the *M. circinelloides* probe hybridized with the *M. rouxii* DNA and the *M. plumbeus* probe hybridized with the *M. racemosus* DNA. However, the *M. rouxii* probe did not hybridize with *M. circinelloides* DNA, nor did the *M. racemosus* probe hybridize with *M. plumbeus* DNA. Therefore, by a process of elimination, each species can be correctly identified. Empty boxes in Table 5 represent zero probe reactivity.

TABLE 5

Zygomyces Probes

| FUNGUS | D-probes | | | | | | | | | | | |
|---|---|---|---|---|---|---|---|---|---|---|---|---|
| | RORY | RMIC | RCIR | RSTOL | RPUS | MRACE | MCIR | MRX | MPLUM | MIND | ABS | CUN |
| R. oryzae (n = 5) | 1.50 ± 0.48 | | | | 0.01 | | | | | | | |
| R. microsporus (n = 5) | | 0.96 ± 0.61 | | | | | | | | | | |
| R. circinans (n = 3) | | | 1.56 ± 0.19 | | | | | | | | | |
| R. stolonifer (n = 5) | | | | 2.53 ± 0.07 | | | 0.01 | | | | | |
| Rhizomucor pusillus (n = 2) | | | | | 1.10 ± 0.68 | | | | | | | |
| M. racemosus (n = 6) | | | | | 0.01 | 2.02 ± 0.34 | | | 0.29 ± 0.52 | | | |
| M. circinelloides (n = 3) | | | | | | | 1.63 ± 0.37 | 0.01 | 0.02 | | | |
| M. rouxii (n = 1) | | | | | | | 1.77 | 0.76 | | | | |
| M. plumbeus (n = 2) | | | | | | | | | 2.14 ± 0.25 | | | |
| M. indicus (n = 1) | | 0.01 | | | | | | | | 1.70 ± 0.04 | | |

TABLE 5-continued

Zygomyces Probes

D-probes

| FUNGUS | RORY | RMIC | RCIR | RSTOL | RPUS | MRACE | MCIR | MRX | MPLUM | MIND | ABS | CUN |
|---|---|---|---|---|---|---|---|---|---|---|---|---|
| *Absidia corymbifera* (n = 2) | | | | | 0.01 | | | | | 0.01 | 1.61 ± 0.08 | |
| *Cunninhamella elegans* (n = 2) | | 0.01 | | | | | | | | | | 2.26 ± 0.03 |
| Negative control | | | | | | | | | | | | |
| *A. fumigatus* | | | | | | | | | | 0.01 | 0.02 | |
| *A. flavus* | | | | | 0.01 | | | | | | 0.05 | |
| *A. niger* | | | | | | | | 0.01 | | | | |
| *A. nidulans* | | | | | | | | | | 0.01 | 0.01 | |
| *A. terreus* | 0.01 | | | | | | | | | | | |
| *A. parasiticus* | | | | | 0.01 | | | | | | 0.03 | |
| *A. clavatus* | | | | | | | | | | | 0.02 | |
| *P. marneffei* | | | 0.01 | | | | | | | | | |
| *P. notatum* | | | | | | | | | | | 0.03 | |
| *F. oxysporum* | | | | | | | | | 0.01 | | | |
| *F. solani* | | | | | | | | | | | | |
| *F. moniliforme* | 0.01 | | | 0.01 | | | | | 0.01 | | 0.01 | |
| *P. boydii* | 0.02 | | | | | | | | | | | |
| *Sporothrix schenckii* | | | | | | | | | | | | |
| *C. albicans* | | | | | | | | | | | | |
| *C. tropicalis* | | | | | | | | | | | | |
| *C. krusei* | | | | | | | | | | | | |
| *C. parasilosis* | | | | | | | | | | | | |
| *C. glabrata* | | | | | | | | | | | | |
| *Neosartorya fischeri* | | | 0.01 | | | | | | | | | |
| *Blastomyces dermatitidis* | | | | | | | | | | | | |
| *Apophysomyces elegans* | | | | | | | | | | | | |
| Average | 0.001 ± .004 | 0.001 ± 0.02 | 0.000 ± 0.002 | 0.000 ± 0.003 | 0.001 ± 0.003 | 0.001 ± 0.002 | 0.001 ± 0.002 | 0.001 ± 0.003 | 0.003 ± 0.005 | 0.005 ± 0.01 | 0.001 ± 0.001 | |

Species-specific probes to various other fungi are presented in Table 6, showing correct identification of each species and no false positives. Empty boxes in Table 6 represent zero probe reactivity.

TABLE 6

Pseudallescheria and Sporothrix Probes

| Fungus | *P. boydii* | *P. marneffei* | *P. notatum* | *Sporothrix schenckii* |
|---|---|---|---|---|
| *P. boydii* (n = 4) | 1.65 ± 0.48 | | | |
| *P. marneffei* (n = 3) | 0.01 | 1.24 ± 0.12 | | |
| *P. notatum* (n = 3) | | | 1.93 ± 0.25 | |
| *Sporothrix schenckii* (n = 3) | 0.01 | | | 1.94 ± 0.25 |
| Negative control | | | | |
| *A. fumigatus* | 0.01 | | | |
| *A. flavus* | | | | |
| *A. niger* | | | | |
| *A. nidulans* | | | | |
| *A. terreus* | | | | |
| *A. parasiticus* | | | | |
| *A. clavatus* | | | | 0.11 |
| *F. oxysporum* | | 0.10 | | |
| *F. solani* | | 0.14 | | |
| *F. moniliforme* | | 0.08 | | |
| *R. oryzae* | 0.01 | | | |
| *R. microsporus* | 0.01 | | | |

TABLE 6-continued

Pseudallescheria and Sporothrix Probes

| Fungus | P. boydii | P. marneffei | P. notatum | Sporothrix schenckii |
|---|---|---|---|---|
| R. circinans | 0.01 | | | |
| R. stolonifer | 0.01 | | | |
| Rhizomucor pusilus | | | | |
| M. racemosus | | 0.04 | | |
| M. circinelloides | 0.01 | 0.09 | | |
| M. rouxii | 0.01 | | | |
| M. plumbeus | | 0.05 | | |
| M. indicus | | | | |
| Absidia corymbifera | 0.01 | | | |
| Cunninghamela bertholletiae | 0.01 | | | |
| C. albicans | | | | |
| C. tropicalis | | 0.02 | | |
| C. krusei | | | | |
| C. parasilosis | | | | |
| C. glabrata | | | | |
| Neosatorya pseudofischeri | | 0.03 | | |
| Blastomyces dermatitidis | 0.01 | | | |
| Apophysomyces elegans | 0.01 | | | |
| Average Negative Controls | 0.004 ± 0.002 | 0.013 ± 0.03 | 0.002 ± 0.019 | 0.001 ± 0.002 |

All of the references mentioned in this Specification are hereby incorporated by reference in their entirety.

REFERENCES

1. Ampel, N. M. 1996. Emerging disease issues and fungal pathogens associated with HIV infection. Emerg. Infec. Dis. 2:109–116.
2. Andriole, V. T. 1996. *Aspergillus* infections: problems in diagnosis and treatment. Infect. Agents and Dis. 5:47–54.
3. Andriole, V. T. 1993. Infections with *Aspergillus* species. Clin. Infec. Dis. 17 Suppl 2:S481–S486.
4. Bir, N., A. Paliwal, K. Muralidhar, P. Reddy, and P. U. Sarma. 1995. A rapid method for the isolation of genomic DNA from *Aspergillus fumigatus*. Prep. Biochem. 25:171–181.
5. Blum, U., M. Windfuhr, C. Buitrago-Tellez, G. Sigmund, E. W. Herbst, and M. Langer. 1994. Invasive pulmonary aspergillosis. MRI, CT, and plain radiographic findings and their contribution for early diagnosis. Chest 106: 1156–1161.
6. Caillot, D., O. Casasnovas, A. Bernard, J. F. Couaillier, C. Durand, B. Cuisenier, E. Solary, F. Piard, T. Petrella, A. Bonnin, G. Couaillault, M. Dumas, and H. Guy, 1997. Improved management of invasive pulmonary aspergillosis in neutropenic patients using early thoracic computed tomographic scan and surgery. J. Clin. Oncol. 15:139–147.
7. Denning, D. W. Therapeutic outcome in invasive aspergillosis. Clin. Infect. Dis. 23:608–615.
8. Denning, D. W. Diagnosis and management of invasive aspergillosis. Curr. Clin. Topics Inf. Dis. 16:277–299.
9. de Repentigny, L., L. Kaufman, G. T. Cole, D. Kruse, J. P. Latge, and R. C. Matthews. 1994. Immunodiagnosis of invasive fungal infections. J. Med. Vet. Mycol. 32 Suppl 1239–252.
10. Dupont, B., D. W. Denning, D. Marriott, A. Sugar, M. A. Viviani, and T. Sirisanthana. 1994. Mycoses in AIDS patients. J. Med. Vet. Mycol. 32 Suppl 1:221–239.
11. Fisher, B. D., D. Armstrong, B. Yu, and J. W. M. Gold. 1981. Invasive aspergillosis: progress in early diagnosis and treatment. Am. J. Med. 71:571–577.
12. Fridkin, S. K. and W. R. Jarvis. 1996. Epidemiology of nosocomial fungal infections. Clin. Microbiol. Rev. 9:499–511.
13. Fujita, S-I., B. A. Lasker, T. J. Lott, E. Reiss, and C. J. Morrison. 1995. Micro titration plate enzyme immunoassay to detect PCR-amplified DNA from *Candida* species in blood. J. Clin. Microbiol. 33:962–967.
14. Gordon, M. A., E. W. Lapa, and J. Kane. 1977. Modified indirect fluorescent antibody test for aspergillosis. J. Clin. Microbiol. 6:161–165.
15. Holmes, A. R., R. D. Cannon, M. G. Shepard, and H. F. Jenkinson. 1994. Detection of *Candida albicans* and other yeast in blood by PCR. J. Clin. Microbiol. 32:228–231.
16. Hung, C. C., S. C. Chang, P. C. Yang, W. C. Hseigh. 1994. Invasive pulmonary pseudallescheriasis with direct invasion of the thoracic spine in an immunocompromised patient. Eur. J. Clin. Microbiol. Infect. Dis. 13:749–751.
17. Kappe, R., and H. P. Seeliger. 1993. Serodiagnosis of deep-seated fungal infections. Curr. Topics Med. Mycol. 5:247–280.
18. Kappe, R., A. Schulze-Berge, H. G. Sonntag. 1996. Evaluation of eight antibody tests and one antigen test for the diagnosis of invasive aspergillosis. Mycoses 39:13–23.
19. Kaufman and Reiss, Manual of Clinical Microbiology.
20. Kremery, V., Jr., E. Kunova, Z. Jesenska, J. Trupl, S. Spanik, J. Mardiak, M. Studena, and E. Kukuckova. 1996. Invasive mold infections in cancer patients: 5 years' experience with *Aspergillus, Mucor, Fusarium* and *Acremonium* infections. Supportive Care in Cancer 4:39–45.
21. Khoo, S. H., and D. W. Denning. 1994. Invasive aspergillosis in patients with AIDS. Clin. Infect. Dis 19 Suppl 1: S41–S48.
22. Kwok, S., and R. Higuichi. 1989. Avoiding false positives with PCR. Nature (London) 339:237–238.
23. Larone, D. H. Medically Important Fungi: A Guide to Identification. 3rd ed. ASM Press, Washington, D.C. 1995.
24. Leenders, A., A. van Belkum, S. Janssen, S. de Marie, J. Kluytmans, J. Wielenga, B. Lowenberg, and H. Verbrugh.

Molecular epidemiology of apparent outbreak of invasive aspergillosis in a hematology ward. J. Clin. Microbiol. 34:345–351.

25. Makimura, K., S. Y. Murayama, H. Yamaguchi. 1994. Specific detection of *Aspergillus* and *Penicillium* species from respiratory specimens by polymerase chain reaction (PCR). Jap. J. Med. Sci. Biol. 47:141–156.
26. Maniatis, T., E. F. Fritsch, and J. Sambrook. 1982. Molecular cloning: a laboratory manual. Cold Spring Harbor Laboratory, Cold Spring Harbor, N.Y.
27. Martino, P., and C. Girmenia. 1993. Diagnosis and treatment of invasive fungal infections in cancer patients. Supportive Care in Cancer. 1:240–244.
28. Melchers, W. J., P. E. Verweij, P. van den Hurk, A. van Belkum, B. E. De Pauw, J. A. Hoogkamp-Korstanje, and J. F. Meis. 1994. General primer-mediated PCR for detection of *Aspergillus* species. J. Clin. Microbiol. 32:1710–1717.
29. Miller, W. T. J., G. J. Sals, I. Frank, W. B. Gefter, M. Aronchick, W. T. Miller. 1994. Pulmonary aspergillosis patients with AIDS. Clinical and radiographic correlations. Chest 105:37–44.
30. Miyakawa, Y., T. Mabuchi, and Y. Fukazawa. 1993. New method for detection of *Candida albicans* in human blood by polymerase chain reaction. J. Clin. Microbiol. 31:3344–3347.
31. Montone, K. T., and L. A. Litzky. 1995. Rapid method for detection of *Aspergillus* 5S ribosomal RNA using a genus-specific oligonucleotide probe. J. Clin. Microbiol. 103:48–51.
32. Rogers, T. R., K. A. Haynes, and R. A. Barnes. 1990. Value of antigen detection in predicting invasive aspergillosis. Lancet 336:1210–1213.
33. Sandhu, G. S., B. C. Kline, L. Stockman, and G. D. Roberts,. 1995. Molecular probes for diagnosis of fungal infections. J. Clin. Microbiol. 33:2913–2919.
34. Shin, J. H., F. S. Nolte, and C. J. Morrison. 1997. Rapid identification of *Candida* species in blood cultures using a clinically useful PCR method. J. Clin. Microbiol. in press.
35. Tang, C. M., D. W. Holden, A. Aufauvre-Brown, and J. Cohen. The detection of *Aspergillus* spp. by the polymerase chain reaction and its evaluation in bronchoalveolar lavage fluid. Amer. Rev. Respir. Dis 148:1313–1317.
36. Thompson, B. H., W. Stanford, J. R. Galvin, and Y. Kurlhara. 1995. Varied radiologic appearances of pulmonary aspergillosis. Radiographics 15:1273–1284.
37. Tierney, Jr. L. M. Aspergillosis. In Current Medical Diagnosis and Treatment. 33rd ed. Norwalk, Conn.: Appleton and Lange, 1994.
38. Verweij, P. E., J. P. Latge, A. J. Rijs, W. J. Melchers, B. E. De Pauw, J. A. Hoogkamp-Korstanje, and J. F. Mels. 1995. Comparison of antigen detection and PCR assay using bronchoalveolar lavage fluid for diagnosing invasive pulmonary aspergillosis in patients receiving treatment for hematological malignancies. J. Clin. Microbiol. 33:3150–3153.
39. von Eiff, M., N. Roos, R. Schulten, M. Hesse, M. Zuhisdorf, and J. van de Loo. 1995. Pulmonary aspergillosis: early diagnosis improves survival. Respiration 62:341–347.
40. von Eiff, M., N. Roos, W. Fegeler, C. von Eiff, R. Schulten, M. Hesse, M. Zuhisdorf, and J. van de Loo. 1996. Hospital acquired *Candida* and *Aspergillus* pneumonia—diagnostic approaches and clinical findings. J. Hosp. Infect. 32:17–28.
41. Walsh, T. J. 1993. Management of immunocompromised patients with evidence of an invasive mycosis. Hemat. Oncol. Clin. N .Amer. 7:1003–1026.
42. Walsh, T. J., C. Gonzalez, C. A. Lyman, S. J. Chanock, and P. A. Pizzo. 1996. Invasive fungal infections in children: recent advances in diagnosis and treatment. Adv. Ped. Inf. Dis. 11:187–290.
43. Walsh, T. J., B. De Pauw, E. Anaissle, and P. Martino. 1994. Recent advances in the epidemiology, prevention, and treatment of invasive fungal infections in neutropenic patients. J. Med. Vet. Mycol. 32 Supp 1:33–51.
44. Warnock, D. W. 1995. Fungal complications of transplantation: diagnosis, treatment, and prevention. J. Antimicrob. Chemother. 36 Suppl B:73–90.
45. Yamakami, Y., A. Hashimoto, I. Tokimatsu, and M. Nasu. 1996. PCR detection of DNA specific for *Aspergillus* species in serum of patients with invasive aspergillosis. J. Clin. Microbiol. 34:2464–2468.
46. Young, R. C., and J. E. Bennett. 1971. Invasive aspergillosis: absence of detectable antibody response. Am. Rev. Respir. Dis 104:710–716.
47. Zervos, M. J. and J. A. Vasquez. 1996. DNA analysis in the study of fungal infections in the immunocompromised host. Clin. Lab. Med. 16:73–88.

We claim:

1. A method of detecting a species of *Fusarium* in a sample, comprising
contacting the sample with a nucleic acid probe consisting of SEQ ID NO: 49, SEQ ID NO: 50 or SEQ ID NO: 51 or the complement thereof;
wherein hybridization of the nucleic acid probe with the sample indicates the detection of a species of *Fusarium* in the sample.

2. The method of claim 1, wherein the probe selectively hybridizes with a nucleic acid sequence set forth as SEQ ID NO: 6, or the complement thereof, and wherein the species of *Fusarium* is *Fusarium solani*.

3. The method of claim 1, wherein the probe selectively hybridizes with a nucleic acid sequence set forth as SEQ ID NO: 7, or the complement thereof, and wherein the species of *Fusarium* is *Fusarium moniliforme* in the sample.

4. The method of claim 1, wherein the probe consists of a nucleic acid sequence having a sequence as set forth as SEQ ID NO: 49, and where the species of *Fusarium* is *Fusarium moniliforme*.

5. The method of claim 1, wherein the probe consists of a nucleic acid sequence having a sequence as set forth as SEQ ID NO: 50, and where the species of *Fusarium* is *Fusarium oxysporum*.

6. The method of claim 1, wherein the probe consists of a nucleic acid sequence having a sequence as set forth as SEQ ID NO: 51, and where the species of *Fusarium* is *Fusarium solani*.

7. The method of claim 1, wherein the probe is labeled.

8. The method of claim 7, wherein the label is a radioactive label, an enzymatic label or a fluorescent label.

9. An isolated nucleic acid probe consisting of a nucleic acid sequence as set forth as SEQ ID NO: 49, SEQ ID NO: 50, or SEQ ID NO: 51.

10. The isolated nucleic acid probe of claim 9, wherein the probe consists of a nucleic acid sequence having a sequence as set forth as SEQ ID NO: 49.

11. The isolated nucleic acid probe of claim 9, wherein the probe consists of a nucleic acid sequence having a sequence as set forth as SEQ ID NO: 50.

12. The isolated nucleic acid probe of claim 9, wherein the probe consists of a nucleic acid sequence having a sequence as set forth as SEQ ID NO: 51.

13. The isolated nucleic acid probe of claim 9, wherein the probe is labeled.

14. The isolated nucleic acid probe of claim 13, wherein the label is a radioactive label, an enzymatic label or a fluorescent label.

15. An isolated nucleic acid sequence comprising a sequence as set forth as SEQ ID NO: 6 or SEQ ID NO: 7.

16. An isolated nucleic acid sequence consisting essentially of a sequence as set forth as SEQ ID NO: 6 or SEQ ID NO: 7.

17. The isolated nucleic acid of claim 15, comprising a nucleic acid sequence set forth as SEQ ID NO: 6.

18. The isolated nucleic acid sequence of claim 15, comprising a nucleic acid sequence set forth as SEQ ID NO: 7.

19. The isolated nucleic acid of claim 16, consisting of a nucleic acid sequence set forth as SEQ ID NO: 6.

20. The isolated nucleic acid of claim 16, consisting of a nucleic acid sequence set forth as SEQ ID NO: 7.

* * * * *

SEQUENCE LISTING

<160> NUMBER OF SEQ ID NOS: 61

<210> SEQ ID NO 1
<211> LENGTH: 208
<212> TYPE: DNA
<213> ORGANISM: Aspergillus flavus

<400> SEQUENCE: 1

```
gctgcccatc aagcacggct tgtgtgttgg gtcgtcgtcc cctctccggg ggggacgggc      60
cccaaaggca gcggcggcac cgcgtccgat cctcgagcgt atgggctttt gtcaccgct     120 ctgtaggccc ggccggcgct tgccgaacgc aaatcaatct ttttccaggt tgacctcgga    180
tcaggtaggg atacccgctg aacttcaa                                       208
```

<210> SEQ ID NO 2
<211> LENGTH: 364
<212> TYPE: DNA
<213> ORGANISM: Aspergillus fumigatus

<400> SEQUENCE: 2

```
aaactttcaa caatggatct cttggttccg gcatcgatga agaacgcagc gaaatgcgat      60
aactaatgtg aattgcagaa ttcagtgaat catcgagtct ttgaacgcac attgcgcccc     120
ctggtattcc gggggggcatg cctgtccgag cgtcattgct gcccatcaag cacggcttgt    180
gtgttgggcc cccgtccccc tctcccgggg acgggcccg aaaggcagcg gcggcaccgc      240
gtccggtcct cgagcgtatg ggcttgtca cctgctctgt aggcccggcc ggcgccagcc      300
gacacccaac tttattttc taaggttgac ctcggatcag gtagggatac ccgctgaact      360
taaa                                                                   364
```

<210> SEQ ID NO 3
<211> LENGTH: 365
<212> TYPE: DNA
<213> ORGANISM: Aspergillus niger

<400> SEQUENCE: 3

```
aaactttcaa caatggatct cttggttccg gcatcgatga agaacgcagc gaaatgcgat      60
aactaatgtg aattgcagaa ttcagtgaat catcgagtct ttgaacgcac attgcgcccc     120
ctggtattcc gggggggcatg cctgtccgag cgtcattgct gccctcaagc acggcttgtg    180
tgttgggtcg ccgtcccct ctcccggggg acgggcccga aaggcagcgg cggcaccgcg      240
tccgatcctc gagcgtatgg ggctttgtca cctgctctgt aggcccggcc ggcgcctgcc     300
gacgttatcc aaccattttt ttccaggttg acctcggatc aggtagggat acccgctgaa    360
cttaa                                                                   365
```

<210> SEQ ID NO 4
<211> LENGTH: 355
<212> TYPE: DNA
<213> ORGANISM: Aspergillus terreus

<400> SEQUENCE: 4

```
aaactttcaa caatggatct cttggttccg gcatcgatga agaacgcagc gaaatgcgat      60
aactaatgtg aattgcagaa ttcagtgaat catcgagtct ttgaacgcac attgcgcccc     120
ctggtattcc gggggggcat gcctgtccga gcgtcattgc tgccctcaag cccggcttgt     180
gtgttgggcc ctcgtccccc ggctcccggg ggacgggccc gaaaggcagc ggcggcaccg     240
cgtccggtcc tcgagcgtat ggggcttcgt cttccgctcc gtaggcccgg ccggcgcccg    300
ccgaacgcat ttatttgcaa cttgtttttt tttccaggtt gacctcggat caggt          355
```

<210> SEQ ID NO 5
<211> LENGTH: 365
<212> TYPE: DNA
<213> ORGANISM: Aspergillus nidulans

<400> SEQUENCE: 5

```
aaactttcaa caatggatct cttggttccg gcatcgatga agaacgcagc gaactgcgat      60
aagtaatgtg aattgcagaa ttcagtgaat catcgagtct ttgaacgcac attgcgcccc     120
ctggcattcc gggggggcatg cctgtccgag cgtcattgct gccctcaagc ccggcttgtg    180
```

```
tgttgggtcg tcgtccccccc ccccgggggga cgggcccgaa aggcagcggc ggcaccggtc    240
cggtcctcga gcgtatgggg cttggtcacc cgctcgatta gggccggccg ggcgccagcc    300
ggcgtctcca accttatctt tctcaggttg acctcggatc aggtagggat acccgctgaa    360
cttaa                                                                365

<210> SEQ ID NO 6
<211> LENGTH: 319
<212> TYPE: DNA
<213> ORGANISM: Fusarium solani

<400> SEQUENCE: 6
gaaaatgcga taagtaatgt gaattgcaga attcagtgaa tcatcgaatc tttgaacgca    60
cattgcgccc gccagtattc tggcgggcat gcctgttcga gcgtcattac aaccctcagg    120
cccccgggcc tggcgttggg gatcggcgga agcccctgc gggcacaacg ccgtccccca    180
aatacagtgg cggtcccgcc gcagcttcca ttgcgtagta gctaacacct cgcaactgga    240
gagcggcgcg gccacgccgt aaaacaccca acttctgaat gttgacctcg aatcaggtag    300
gaatacccgc tgaacttaa                                                  319

<210> SEQ ID NO 7
<211> LENGTH: 310
<212> TYPE: DNA
<213> ORGANISM: Fusarium moniliforme

<400> SEQUENCE: 7
aaatgcgata agtaatgtga attgcaaaat tcagtgaatc atcgaatctt tgaacgcaca    60
ttgcgcccgc cagtattctg gcgggcatgc ctgttcgagc gtcatttcaa ccctcaagcc    120
cccgggtttg gtgttgggga tcggcaagcc cttgcggcaa gccggccccg aaatctagtg    180
gcggtctcgc tgcagcttcc attgcgtagt agtaaaaccc tcgcaactgg tacgcggcgc    240
ggccaagccg ttaaaccccc aacttctgaa tgttgacctc ggatcaggta ggaatacccg    300
ctgaacttaa                                                            310

<210> SEQ ID NO 8
<211> LENGTH: 330
<212> TYPE: DNA
<213> ORGANISM: Mucor rouxii

<400> SEQUENCE: 8
aaagtgcgat aactagtgtg aattgcatat tcagtgaatc atcgagtctt tgaacgcaac    60
ttgcgctcat tggtattcca atgagcacgc ctgtttcagt atcaaaacaa accctctatc    120
cagcattttg ttgaatagga atactgagag tctcttgatc tattctgatc tcgaacctct    180
tgaaatgtac aaaggcctga tcttgtttaa atgcctgaac ttttttttaa tataaagaga    240
agctcttgcg gtaaactgtg ctggggcctc ccaaataata ctcttttttaa atttgatctg    300 aaatcaggcg ggattacccg ctgaacttaa                                      330

<210> SEQ ID NO 9
<211> LENGTH: 328
<212> TYPE: DNA
<213> ORGANISM: Mucor racemosus

<400> SEQUENCE: 9
aaagtgcgat aactagtgtg aattgcatat tcagtgaatc atcgagtctt tgaacgcaac    60
ttgcgctcat tggtattcca atgagcacgc ctgtttcagt atcaaaacaa accctctatc    120
```

-continued

```
caactttgt tgtataggat tattgggggc ctctcgatct gtatagatct tgaaatccct      180
gaaatttact aaggcctgaa cttgtttaaa tgcctgaact tttttttaat ataaaggaaa     240
gctcttgtaa ttgactttga tggggcctcc caaataaatc tcttttaaat ttgatctgaa     300
atcaggcggg attacccgct gaacttaa                                        328

<210> SEQ ID NO 10
<211> LENGTH: 327
<212> TYPE: DNA
<213> ORGANISM: Mucor plumbeus

<400> SEQUENCE: 10
aaagtgcgat aactagtgtg aattgcatat tcagtgaatc atcgagtctt tgaacgcaac     60
ttgcgctcat tggtattcca atgagcacgc ctgtttcagt atcaaaacaa accctctatc    120 caactttgt tgtataggat tattgggggc ctctcgatct gtatagatct tgaaacccctt    180 gaaatttact aaggcctgaa cttgtttaat gcctgaactt ttttttaata taaaggaaag    240
ctcttgtaat tgactttgat ggggcctccc aaataaatct ttttttaaatt tgatctgaaa   300 tcaggtggga ttacccgctg aacttaa                                        327

<210> SEQ ID NO 11
<211> LENGTH: 322
<212> TYPE: DNA
<213> ORGANISM: Mucor indicus

<400> SEQUENCE: 11
aaagtgcgat aactagtgtg aattgcatat tcagtgaatc atcgagtctt tgaacgcatc     60
ttgcactcaa tggtattcca ttgagtacgc ctgtttcagt atcaaaaaca acccttattc    120
aaaattcttt ttttgaatag atatgagtgt agcaaccta caagttgaga cattttaaat    180
aaagtcaggc catatcgtgg attgagtgcc gatactttt taattttgaa aaggtaaagc     240
atgttgatgt ccgcttttttg ggcctcccaa ataactttt aaacttgatc tgaaatcagg    300
tgggattacc cgctgaactt aa                                             322

<210> SEQ ID NO 12
<211> LENGTH: 330
<212> TYPE: DNA
<213> ORGANISM: Mucor circinelloides f.

<400> SEQUENCE: 12
aaagtgcgat aactagtgtg aattgcatat tcagtgaatc atcgagtctt tgaacgcaac     60
ttgcgctcat tggtattcca atgagcacgc ctgtttcagt atcaaaacaa accctctatc    120
caacattttt gttgaatagg atgactgaga gtctcttgat ctattctgat ctcgaagctc    180
ttgaaatgta caaggcctg atcttgtttg aatgcctgaa ctttttttta atataaagag    240
aagctcttgc ggtaaactgt gctggggcct cccaaataac acatctttaa atttgatctg    300
aaatcaggtg ggactacccg ctgaacttaa                                     330

<210> SEQ ID NO 13
<211> LENGTH: 333
<212> TYPE: DNA
<213> ORGANISM: Rhizopus oryzae

<400> SEQUENCE: 13
agtgcgataa ctagtgtgaa ttgcatattc agtgaatcat cgagtctttg aacgcagctt     60
```

```
gcactctatg gttttctat agagtacgcc tgcttcagta tcatcacaaa cccacacata      120
acatttgttt atgtggtgat gggtcgcatc gctgttttat tacagtgagc acctaaaatg     180
tgtgtgattt tctgtctggc ttgctaggca ggaatattac gctggtctca ggatcttttt    240
ttttggttcg cccaggaagt aaagtacaag agtataatcc agtaacttc aaactatgat      300 ctgaagtcag gtgggattac ccgctgaact taa                                  333
```

<210> SEQ ID NO 14
<211> LENGTH: 333
<212> TYPE: DNA
<213> ORGANISM: Rhizopus oryzae

<400> SEQUENCE: 14

```
agtgcgataa ctagtgtgaa ttgcatattc agtgaatcat cgagtctttg aacgcagctt      60
gcactctatg gttttctat agagtacgcc tgcttcagta tcatcacaaa cccacacata      120
acatttgttt atgtggtaat gggtcgcatc gctgttttat tacagtgagc acctaaaatg     180
tgtgtgattt tctgtctggc ttgctaggca ggaatattac gctggtctca ggatcttttt    240
ctttggttcg cccaggaagt aaagtacaag agtataatcc agcaactttc aaactatgat     300
ctgaagtcag gtgggattac ccgctgaact taa                                  333
```

<210> SEQ ID NO 15
<211> LENGTH: 348
<212> TYPE: DNA
<213> ORGANISM: Rhizopus microsporus

<400> SEQUENCE: 15

```
aaagtgcgat aactagtgtg aattgcatat tcgtgaatca tcgagtcttt gaacgcagct      60
tgcactctat ggatcttcta tagagtacgc ttgcttcagt atcataacca acccacacat     120
aaaatttatt ttatgtggtg atggacaagc tcggttaaat ttaattatta taccgattgt     180
ctaaaataca gcctctttgt aattttcatt aaattacgaa ctacctagcc atcgtgcttt     240
tttggtccaa ccaaaaaaca tataatctag gggttctgct agccagcaga tattttaatg    300
atctttaact atgatctgaa gtcaagtggg actacccgct gaacttaa                  348
```

<210> SEQ ID NO 16
<211> LENGTH: 349
<212> TYPE: DNA
<213> ORGANISM: Rhizopus microsporus

<400> SEQUENCE: 16

```
aaagtgcgat aactagtgtg aattgcatat tcgtgaatca tcgagtcttt gaacgcagct      60
tgcactctat ggatcttcta tagagtacgc ttgcttcagt atcataacca acccacacat     120
aaaatttatt ttatgtggtg atggacaagc tcggttaaat ttaattatta taccgattgt     180
ctaaaataca gcctctttgt aattttcatt aaattacgaa ctacctagcc atcgtgcttt     240
tttggtccaa ccaaaaaaca tataatctag gggttctgct agccagcaaa tattttaatg    300
atctttaacc tatgatctga agtcaagtgg gactacccgc tgaacttaa                 349
```

<210> SEQ ID NO 17
<211> LENGTH: 361
<212> TYPE: DNA
<213> ORGANISM: Rhizopus circinans

<400> SEQUENCE: 17

```
aaattgcgat aactagtgtg aattgcattt tcagtgaatc atcgagtctt tgaacgcatc      60
```

-continued

```
ttgcgctctt gggattcttc cctagagcac acttgcttca gtatcataac aaaaccctca    120
cctaatattt tttttttta aaaaaaaat attagagtgg tattggggtc tctttggtaa     180
ttctttgtaa ttataaaagt acccttaaat gtcataaaca ggttagcttt agcttgcctt    240
taaagatctt cttagggtat cattactttt cgtaaatctt aataggcct gtcacataat     300 tctacccttaa aatttcttaa accttgatct gaagtcaagt gggagtaccc gctgaactta   360
a                                                                    361
```

<210> SEQ ID NO 18
<211> LENGTH: 360
<212> TYPE: DNA
<213> ORGANISM: Rhizopus circinans

<400> SEQUENCE: 18

```
aaattgcgat aactagtgtg aattgcattt tcagtgaatc atcgagtctt tgaacgcatc    60
ttgcgctctt gggattcttc cctagagcac acttgcttca gtatcataac aaaaccctca   120
cctaatattt tttttaaaa aaaaaaata ttagagtggt attggggtct ctttggtaat     180
tctttgtaat tataaaagta cccttaaatg tcataaacag gttagcttta gcttgccttt    240
aaagatcttc ttagggtatc attacttttc gtaaatcttt aataggcctg tcacataatt    300
ctacccttaa atttcttaaa ccttgatctg aagtcaagtg ggagtacccg ctgaacttaa    360
```

<210> SEQ ID NO 19
<211> LENGTH: 486
<212> TYPE: DNA
<213> ORGANISM: Rhizopus stolonifer

<400> SEQUENCE: 19

```
aaagtgcgat aactagtgtg aattgcatat tcagtgaatc atcgagtctt tgaacgcaac    60
ttgcactcta tggttttccg taaagtacgc ttgcttcagt atcataaaga cccccatcctg  120 attattattt ttttattaaa ataattaatt ttggagataa taaaaatgag gctctttctt   180
ttcttttttt ttttttttaaa aaaaggggg ggaaagggtc ttttaaaatg ggcaaattct    240 gggttttta ctaaacctga actccccca aaaattcaaa aaaaaaaaa tgggttttac     300 caaatttttt tttttttct ccttttttgtg tagttaatac tctattaaat ttatttactt    360
ggtattataa cgattatgca agaagggaga gaacaaagaa taatgaaaga gagttttaa    420 ataaattctt ttttcatttt ttcaatcaat gatctgaagt caagtgggat acccgctgaa   480
acttaa                                                              486
```

<210> SEQ ID NO 20
<211> LENGTH: 349
<212> TYPE: DNA
<213> ORGANISM: Rhizomucor pusillus

<400> SEQUENCE: 20

```
aaattgcgaa aagtaatgcg atctgcagcc tttgcgaatc atcgaattct cgaacgcacc    60
ttgcacccct tggttcatcc attgggtacg tctagttcag tatctttatt aaccccctaaa  120 ggtttatttt ttgataaatc tttgatttg cggtgctgat ggattttcat ccgttcaagc    180
tacccgaaca atttgtatgt tgttgaccct tgatatttcc ttgagggctt gcattggtat    240
ctaatttttt accagtgtgc ttcgagatga tcaagtataa aggtcaatca accacaaata    300
aatttcaact atggatctga acttagatgg gattacccgc tgaacttaa                349
```

<210> SEQ ID NO 21
<211> LENGTH: 425
<212> TYPE: DNA
<213> ORGANISM: Absidia corymbifera

<400> SEQUENCE: 21

| | | | | | |
|---|---|---|---|---|---|
| aaagtgcgat | aattattgcg | acttgcattc | atagcgaatc | atcgagttct | cgaacgcatc | 60 |
| ttgcgcctag | tagtcaatct | actaggcaca | gttgtttcag | tatctgcaac | taccaatcag | 120 |
| ttcaacttgg | ttctttgaac | ctaagcgagc | tggaaatggg | cttgtgttga | tggcattcag | 180 |
| ttgctgtcat | ggccttaaat | acatttagtc | ctaggcaatt | ggctttagtc | atttgccgga | 240 |
| tgtagactct | agagtgcctg | aggagcaacg | acttggttag | tgagttcata | attccaagtc | 300 |
| aatcagtctc | ttcttgaact | aggtcttaat | ctttatggac | tagtgagagg | atctaacttg | 360 |
| ggtcttctct | taaaacaaac | tcacatctag | atctgaaatc | aactgagatc | accgctgaa | 420 |
| cttaa | | | | | | 425 |

<210> SEQ ID NO 22
<211> LENGTH: 399
<212> TYPE: DNA
<213> ORGANISM: Absidia corymbifera

<400> SEQUENCE: 22

| | | | | | |
|---|---|---|---|---|---|
| aaagtgcgat | aattattgcg | acttgcattc | atagtgaatc | atcgagttct | gaacgcatc | 60 |
| ttgcgcctag | tagtcaatct | actaggcaca | gttgtttcag | tatctgcatc | caccaatcaa | 120 |
| cttaacctt | tgtgttgagt | tggaactggg | cttctagttg | atggcattta | gttgctgtca | 180 |
| tggccttaaa | tcaatgtcct | aggtgttaga | acatctaaca | ccggatggaa | actttagagc | 240 |
| gctttaagag | cagcttggtt | agtgagttca | ataattccaa | gcattaagtc | ttttaatgaa | 300 |
| ctagcttttc | tatctatggg | acactacttg | gagaaatcca | agtaaccttt | aaactcccat | 360 |
| ttagatctga | aatcaactga | gaccacccgc | tgaacttaa | | | 399 |

<210> SEQ ID NO 23
<211> LENGTH: 359
<212> TYPE: DNA
<213> ORGANISM: Cunninghamella elegans

<400> SEQUENCE: 23

| | | | | | |
|---|---|---|---|---|---|
| aaatcgcgat | atgtaatgtg | actgcctata | gtgaatcatc | aaatctttga | aacgcatctt | 60 |
| gcaccttatg | gtattccata | aggtacgtct | gtttcagtac | cactaataaa | tctctctcta | 120 |
| tccttgatga | tagaaaaaaa | aaaaataatt | tttactgggc | ccggggaatc | cttttttttt | 180 |
| tttaataaaa | aggaccaatt | ttggcccaaa | aaaaggggtt | gaactttttt | taccagatct | 240 |
| tgcatctagt | aaaaacctag | tcggctttaa | tagattttta | ttttctatta | agtttatagc | 300 |
| cattcttata | tttttttaaaa | tcttggcctg | aaatcagatg | ggatacccgc | tgaacttaa | 359 |

<210> SEQ ID NO 24
<211> LENGTH: 346
<212> TYPE: DNA
<213> ORGANISM: Pseudallescheria boydii

<400> SEQUENCE: 24

| | | | | | |
|---|---|---|---|---|---|
| aaatgcgata | agtaatgtaa | attgcaaaat | tcagtgaatc | atcgaatctt | tgaaacgcac | 60 |
| attgcgcccg | gcagtaatct | gccgggcatg | cctgtccgag | cgtcatttca | accctcgaac | 120 |
| ctccgttccc | ttagggaagc | ctagggtcgg | tgttgggcg | ctacggcaag | tcctcgcaac | 180 |

```
ccccgtaggc cctgaaatac agtggcggtc ccgccgcggt tgccttctgc gtagtaagtc    240
tcttttgcaa gctcgcattg ggtcccggcg gaggcctgcc gtcaaaccac ctaacaactc    300
cagatggttt gacctcggat caggtagggt tacccgctga acttaa                   346

<210> SEQ ID NO 25
<211> LENGTH: 346
<212> TYPE: DNA
<213> ORGANISM: Pseudallescheria boydii

<400> SEQUENCE: 25
gaaatgcgat aagtaatgtg aattgcagaa ttcagtgaat catcgaatct ttgaaacgca    60
cattgcgccc ggcagtaatc tgccgggcat gcctgtccga gcgtcatttc aaccctcgaa    120
cctccgtttc ctcagggaag ctcagggtcg gtgttggggc gctacggcaa gtcttcgcaa    180
ccctccgtag gccctgaaat acagtggcgg tcccgccgcg gttgccttct gcgtagaagt    240
ctcttttgca agctcgcatt gggtcccggc ggaggcctgc cgtcaaacca cctataactc    300
caaatggttt gacctcggat caggtagggt tacccgctga acttaa                   346

<210> SEQ ID NO 26
<211> LENGTH: 344
<212> TYPE: DNA
<213> ORGANISM: Scedosporium apiospermum

<400> SEQUENCE: 26
gaaatgcgat aagtaatgtg aattgcagaa ttcagtgaat catcgaatct ttgaacgcac    60
attgcgcccg gcagtaatct gccgggcatg cctgtccgag cgtcatttca accctcgaac    120
ctccgtttcc tcagggaagc tcagggtcgg tgttggggcg ctacggcgag tcttcgcgac    180
cctccgtagg ccctgaaata cagtggcggt cccgccgcgg ttgccttctg cgtagtaagt    240
ctcttttgca agctcgcatt gggtcccggc ggaggcctgc cgtcaaacca cctataactc    300
cagatggttt gacctcggat caggtaggta cccgctgaac ttaa                     344

<210> SEQ ID NO 27
<211> LENGTH: 343
<212> TYPE: DNA
<213> ORGANISM: Scedosporium apiospermum

<400> SEQUENCE: 27
aaatgcgata agtaatgtga attgcagaat tcagtgaatc atcgaatctt tgaacgcaca    60
ttgcgcccgg cagtaatctg ccgggcatgc ctgtccgagc gtcatttcaa ccctcgaacc    120
tccgtttcct cagggaagct cagggtcggt gttggggcgc tacggcgagt cttcgcgacc    180
ctccgtaggc cctgaaatac agtggcggtc ccgccgcggt tgccttctgc gtagtaagtc    240
tcttttgcaa gctcgcattg ggtcccggcg gaggcctgcc gtcaaaccac ctataactcc    300
agatggtttg acctcggatc aggtaggtac ccgctgaact taa                      343

<210> SEQ ID NO 28
<211> LENGTH: 309
<212> TYPE: DNA
<213> ORGANISM: Penicillium notatum

<400> SEQUENCE: 28
aaatgcgata cgtaatgtga attgcaaatt cagtgaatca tcgagtcttt gaacgcacat    60
tgcgccccct ggtattccgg gggcatgcct gtccgagcgt cattgctgcc ctcaagcac    120
```

```
ggcttgtgtg ttgggccccg tcctccgatc ccggggacg ggcccgaaag gcagcggcgg      180
caccgcgtcc ggtcctcgag cgtatggggc tttgtcaccc gctctgtagg cccggccggc      240
gcttgccgat caacccaaat ttttatccag gttgacctcg gatcaggtag ggatacccgc      300
tgaacttaa                                                             309
```

<210> SEQ ID NO 29
<211> LENGTH: 336
<212> TYPE: DNA
<213> ORGANISM: Sporothrix schenckii

<400> SEQUENCE: 29

```
gaaatgcgat actaatgtga attgcagaat tcagcgaacc atcgaatctt tgaacgcaca      60
ttgcgcccgc cagcattctg gcgggcatgc ctgtccgagc gtcatttccc ccctcacgcg     120
ccccgttgcg cgctggtgtt ggggcgccct ccgcctggcg ggggcccccc gaaagcgagt     180
ggcgggccct gtggaaggct ccgagcgcag taccgaacgc atgttctccc ctcgctccgg     240 aggccccccca ggcgccctgc cggtgaaaac gcgcatgacg cgcagctctt tttacaaggt    300
tgacctcgga tcaggtgagg atacccgctg acttaa                              336
```

<210> SEQ ID NO 30
<211> LENGTH: 18
<212> TYPE: DNA
<213> ORGANISM: Aspergillus flavus

<400> SEQUENCE: 30
gcaaatcaat cttttttcc                                                  18

<210> SEQ ID NO 31
<211> LENGTH: 18
<212> TYPE: DNA
<213> ORGANISM: Aspergillus fumigatus

<400> SEQUENCE: 31
gaacgcaaat caatctttt                                                  18

<210> SEQ ID NO 32
<211> LENGTH: 18
<212> TYPE: DNA
<213> ORGANISM: Aspergillus fumigatus

<400> SEQUENCE: 32 ccgacacccca tctttatt                                                  18

<210> SEQ ID NO 33
<211> LENGTH: 18
<212> TYPE: DNA
<213> ORGANISM: Aspergillus niger

<400> SEQUENCE: 33
gacgttatcc aaccattt                                                   18

<210> SEQ ID NO 34
<211> LENGTH: 18
<212> TYPE: DNA
<213> ORGANISM: Aspergillus terreus

<400> SEQUENCE: 34
gcatttattt gcaacttg                                                   18

```
<210> SEQ ID NO 35
<211> LENGTH: 18
<212> TYPE: DNA
<213> ORGANISM: Aspergillus nidulans

<400> SEQUENCE: 35
ggcgtctcca accttatc                                                18

<210> SEQ ID NO 36
<211> LENGTH: 18
<212> TYPE: DNA
<213> ORGANISM: Mucor rouxii

<400> SEQUENCE: 36
gaataggaat actgagag                                                18

<210> SEQ ID NO 37
<211> LENGTH: 15
<212> TYPE: DNA
<213> ORGANISM: Mucor indicus

<400> SEQUENCE: 37
gaaacccttg aaatt                                                   15

<210> SEQ ID NO 38
<211> LENGTH: 18
<212> TYPE: DNA
<213> ORGANISM: Mucor indicus

<400> SEQUENCE: 38
cgtggattga gtgccgat                                                18

<210> SEQ ID NO 39
<211> LENGTH: 21
<212> TYPE: DNA
<213> ORGANISM: Mucor circinelloides f.

<400> SEQUENCE: 39
aacatttttg tgataggat g                                             21

<210> SEQ ID NO 40
<211> LENGTH: 15
<212> TYPE: DNA
<213> ORGANISM: Mucor racemosus

<400> SEQUENCE: 40
gaaatccctg aaatt                                                   15

<210> SEQ ID NO 41
<211> LENGTH: 18
<212> TYPE: DNA
<213> ORGANISM: Rhizopus oryzae

<400> SEQUENCE: 41
gagtataatc cagyaact                                                18

<210> SEQ ID NO 42
<211> LENGTH: 18
<212> TYPE: DNA
<213> ORGANISM: Rhizopus circinans

<400> SEQUENCE: 42
cttagggtat cattactt                                                18
```

-continued

```
<210> SEQ ID NO 43
<211> LENGTH: 18
<212> TYPE: DNA
<213> ORGANISM: Rhizomucor pusillus

<400> SEQUENCE: 43
tccttgaggg cttgcatt                                                 18

<210> SEQ ID NO 44
<211> LENGTH: 18
<212> TYPE: DNA
<213> ORGANISM: Rhizopus stolonifer

<400> SEQUENCE: 44
cttggtatta taacgatt                                                 18

<210> SEQ ID NO 45
<211> LENGTH: 18
<212> TYPE: DNA
<213> ORGANISM: Pseudallescheria boydii

<400> SEQUENCE: 45
aagtctcttt tgcaagct                                                 18

<210> SEQ ID NO 46
<211> LENGTH: 18
<212> TYPE: DNA
<213> ORGANISM: Penicillium notatum

<400> SEQUENCE: 46
gatcaaccca aattttta                                                 18

<210> SEQ ID NO 47
<211> LENGTH: 18
<212> TYPE: DNA
<213> ORGANISM: Penicillium marneffei

<400> SEQUENCE: 47
gggttggtca ccaccata                                                 18

<210> SEQ ID NO 48
<211> LENGTH: 18
<212> TYPE: DNA
<213> ORGANISM: Penicillium marneffei

<400> SEQUENCE: 48
tggtcaccac catattta                                                 18

<210> SEQ ID NO 49
<211> LENGTH: 18
<212> TYPE: DNA
<213> ORGANISM: Fusarium moniliforme

<400> SEQUENCE: 49
tctagtgacg gtctcgct                                                 18

<210> SEQ ID NO 50
<211> LENGTH: 18
<212> TYPE: DNA
<213> ORGANISM: Fusarium oxysporum

<400> SEQUENCE: 50
cgttaattcg cgttcctc                                                 18
```

<210> SEQ ID NO 51
<211> LENGTH: 21
<212> TYPE: DNA
<213> ORGANISM: Fusarium solani

<400> SEQUENCE: 51
ctaacacctc gcaactggag a                                            21

<210> SEQ ID NO 52
<211> LENGTH: 18
<212> TYPE: DNA
<213> ORGANISM: Cunninghamella elegans

<400> SEQUENCE: 52
tagtcggctt taatagat                                                18

<210> SEQ ID NO 53
<211> LENGTH: 18
<212> TYPE: DNA
<213> ORGANISM: Cunninghamella elegans

<400> SEQUENCE: 53
tattaagttt atagccat                                                18

<210> SEQ ID NO 54
<211> LENGTH: 18
<212> TYPE: DNA
<213> ORGANISM: Cunninghamella elegans

<400> SEQUENCE: 54
taagtttata gccattct                                                18

<210> SEQ ID NO 55
<211> LENGTH: 18
<212> TYPE: DNA
<213> ORGANISM: Absidia corymbifera

<400> SEQUENCE: 55
gttgctgtca tggcctta                                                18

<210> SEQ ID NO 56
<211> LENGTH: 18
<212> TYPE: DNA
<213> ORGANISM: Sporothrix schenckii

<400> SEQUENCE: 56
gacgcgcagc tcttttta                                                18

<210> SEQ ID NO 57
<211> LENGTH: 18
<212> TYPE: DNA
<213> ORGANISM: Rhizopus microsporus

<400> SEQUENCE: 57
catataatct agggttc                                                 18

<210> SEQ ID NO 58
<211> LENGTH: 18
<212> TYPE: DNA
<213> ORGANISM: Aspergillus sp.

<400> SEQUENCE: 58

-continued

```
cctcgagcgt atgggget                                              18

<210> SEQ ID NO 59
<211> LENGTH: 18
<212> TYPE: DNA
<213> ORGANISM: Fusarium sp.

<400> SEQUENCE: 59
cccaacttct gaatgttg                                              18

<210> SEQ ID NO 60
<211> LENGTH: 18
<212> TYPE: DNA
<213> ORGANISM: Mucor sp.

<400> SEQUENCE: 60
mtggggcctc ccaaataa                                              18

<210> SEQ ID NO 61
<211> LENGTH: 21
<212> TYPE: DNA
<213> ORGANISM: Artificial Sequence
<220> FEATURE:
<223> OTHER INFORMATION: B-58 biotin probe

<400> SEQUENCE: 61
gaatcatcga rtctttgaac g                                          21
```